United States Patent
Kheifets et al.

(10) Patent No.: US 11,439,687 B2
(45) Date of Patent: Sep. 13, 2022

(54) BLOOD PLASMA FRACTIONS FOR USE IN MUSCLE REGENERATION

(71) Applicant: Alkahest, Inc., San Carlos, CA (US)

(72) Inventors: Viktoria Kheifets, Mountain View, CA (US); Benson Lu, San Francisco, CA (US); Annette Tennstaedt, Redwood City, CA (US)

(73) Assignee: Alkahest, Inc., San Carlos, CA (US)

( * ) Notice: Subject to any disclaimer, the term of this patent is extended or adjusted under 35 U.S.C. 154(b) by 15 days.

(21) Appl. No.: 17/087,898

(22) Filed: Nov. 3, 2020

(65) Prior Publication Data
US 2021/0128693 A1    May 6, 2021

Related U.S. Application Data

(60) Provisional application No. 63/062,735, filed on Aug. 7, 2020, provisional application No. 62/966,953, filed on Jan. 28, 2020, provisional application No. 62/930,336, filed on Nov. 4, 2019.

(51) Int. Cl.
*A61K 38/38* (2006.01)
*A61P 21/00* (2006.01)

(52) U.S. Cl.
CPC .............. *A61K 38/38* (2013.01); *A61P 21/00* (2018.01)

(58) Field of Classification Search
CPC .................................. A61K 38/38; A61P 21/00
See application file for complete search history.

(56) References Cited

U.S. PATENT DOCUMENTS

| | | | |
|---|---|---|---|
| 4,129,648 A | 12/1978 | Collier et al. | |
| 10,245,285 B2 | 4/2019 | Braithwaite et al. | |
| 10,357,513 B2 | 7/2019 | Braithwaite et al. | |
| 10,525,107 B2 | 1/2020 | Bell et al. | |
| 10,688,130 B2 | 6/2020 | Wyss-Coray et al. | |
| 10,874,692 B2 | 12/2020 | Braithwaite et al. | |
| 10,905,717 B2 | 2/2021 | Braithwaite et al. | |
| 10,905,779 B2 | 2/2021 | Braithwaite et al. | |
| 2013/0243879 A1 * | 9/2013 | Mishra | G01N 33/5023 424/530 |
| 2015/0064164 A1 * | 3/2015 | Edwards | A61P 19/00 424/94.64 |
| 2015/0157664 A1 | 6/2015 | Wyss-Coray et al. | |
| 2016/0206657 A1 | 7/2016 | Mishra | |
| 2017/0232118 A1 | 8/2017 | Braithwaite et al. | |
| 2017/0340671 A1 * | 11/2017 | Braithwaite | A61P 35/00 |
| 2018/0110839 A1 | 4/2018 | Bell et al. | |
| 2018/0311280 A1 | 11/2018 | Braithwaite et al. | |
| 2019/0167719 A1 | 6/2019 | Braithwaite et al. | |
| 2019/0282617 A1 | 9/2019 | Braithwaite et al. | |
| 2019/0321449 A1 | 10/2019 | Bell et al. | |
| 2019/0328782 A1 | 10/2019 | Braithwaite et al. | |
| 2020/0129549 A1 | 4/2020 | Castro et al. | |
| 2020/0352994 A1 | 11/2020 | Wyss-Coray et al. | |

FOREIGN PATENT DOCUMENTS

| | | | |
|---|---|---|---|
| WO | WO0059539 A1 | 10/2000 | |
| WO | WO-2007139291 A1 * | 12/2007 | A61K 35/16 |
| WO | WO2013007308 A1 | 1/2013 | |
| WO | WO2015088915 A1 | 6/2015 | |
| WO | WO2017189919 A1 | 11/2017 | |
| WO | WO2018034712 A1 | 2/2018 | |
| WO | WO2018200560 A1 | 11/2018 | |
| WO | WO2020018343 A1 | 1/2020 | |
| WO | WO2020086469 A1 | 4/2020 | |

* cited by examiner

*Primary Examiner* — Sudhakar Katakam
(74) *Attorney, Agent, or Firm* — Mandar A. Joshi; Bret E. Field; Bozicevic, Field & Francis LLP

(57) ABSTRACT

Methods and compositions for treating aging-related diseases as well as muscle recovery, prevention of muscle degeneration, and maintenance of muscle are described. The compositions used in the methods include blood plasma and blood plasma fractions derived from blood plasma with efficacy in treating and/or preventing disease.

8 Claims, 40 Drawing Sheets

Figure 11A

| | Tibialis Anterior | Extensor Digitorum Longus | Gastrocnemius | Soleus | Days After Last Dose Treatment |
|---|---|---|---|---|---|
| 24-month-old mice | *** (non-immobilized) | * (immobilized) | 0.053 (non-immobilized) | n.s. | 3 |
| 22-month-old mice | n.s. | n.s. | * | * | 28 |
| 26-month-old mice | ** | ** | n.s. | * | 10 |
| Young rats | * | 0.079 | n.s. | n.s. | 49 |
| 22-month-old mice | n.s. | n.s. | n.s. | ** | 28 |

BLOOD PLASMA FRACTIONS FOR USE IN MUSCLE REGENERATION

I. CROSS REFERENCE TO RELATED APPLICATIONS

Pursuant to 35 U.S.C. § 119 (e), this application claims priority to the filing date of U.S. Provisional Patent Application No. 62/930,336, filed Nov. 4, 2019; U.S. Provisional Patent Application No. 62/966,953, filed Jan. 28, 2020; and U.S. Provisional Patent Application No. 63/062,735, dated Aug. 7, 2020; the disclosures of which applications are herein incorporated by reference.

II. FIELD OF THE INVENTION

This invention pertains to the prevention and treatment of muscle disease and injury. The invention relates to the use of blood products, such as blood plasma fractions, to treat and/or prevent conditions associated with aging, such as neurocognitive and neurodegenerative disorders.

III. SUMMARY

Skeletal muscle has a high capacity for regeneration, with satellite cells (myogenic stem cells) the source of this capability. (Kang J S, et al., *Curr Opin Clin Nutr Metab Care*, 13(3):243-48 (2010) and Jang Y C, et al., *Cold Spring Harb Symp Quant Biol*. 76:101-11 (2011)). Satellite cells are activated during adult life in response to muscle injury but can be pathologically deregulated in dystrophic disease. (Jang, id.)

Regeneration of skeletal muscle is considered to coordinate through four processes. These include: degeneration of muscle fibers resulting in necrosis; inflammation and invasion of certain inflammatory cells into muscle; regeneration by activation of satellite cells and subsequent differentiation into myoblasts that help to support the formation of new myofibers and also repair existing, surviving muscle fibers; and remodeling/repair where the regenerated fibers mature, and the extracellular matrix is remodeled. (Id.) The regenerative activity of muscle is also tightly linked to metabolism, which can alter these processes. (Id.)

Sarcopenia is the progressive loss of skeletal muscle mass and strength due to aging. (Tabebordbar M, et al., *Annu. Rev. Pathol. Mech. Dis.*, 8:441-75 (2013)). It is a growing health concern globally, affecting around one-quarter of individuals older than 70 years of age, and 40% of individuals older than 80. (Id.) It results in diminished independence, a loss of performance of normal activities of daily living, and a reduced quality of life. (Id.) As we age, the regenerative capacity of skeletal muscle encounters deficits which have been attributed at least in part to a decrease in the number of muscle satellite cells and myonuclei in muscle fibers. (Id. and Brack A S, et al., *Science*, 317:807-810 (2007)). Additionally, the total number and size of myofibers decrease with aging. (Jang, id.)

In addition to aging-related muscle loss and degeneration, muscle function can be diminished by acute physical or chemical injury, ischemia/reperfusion (e.g. organ-transplantation surgery, stroke, hypovolemic shock), contraction-induced damages, inflammatory myopathies, and genetic-related degenerative disease. The latter can include, for example, Duchenne and Becker muscular dystrophies, myotonic dystrophy, limb girdle muscular dystrophy, Emery-Dreifuss muscular dystrophy, congenital muscular dystrophy, and facioscapulohumeral muscular dystrophy. (Id.)

Currently, treatment options for muscle wasting diseases are limited and are concentrated on managing symptoms, often through immune and inflammatory response management. (Id.) There is therefore a need for novel approaches to reversing the effects of muscle injury and degeneration. Although it has been shown that both heterochronic parabiosis between young and old mice and young mouse serum have some efficacy in reducing a myogenic to fibrogenic conversion of certain muscle cells, there remains the need for a more practical, standardized intervention. (Brack, id.). The instant invention addresses these needs by providing specific fractions or products of blood plasma fractionation.

IV. INCORPORATION BY REFERENCE

All publications and patent applications mentioned in this specification are herein incorporated by reference to the same extent as if each individual publication or patent application was specifically and individually indicated to be incorporated by reference.

V. BRIEF DESCRIPTION OF THE DRAWINGS

FIG. 1 is a depiction of one method of pooled blood plasma fractionation. Pooled plasma is cryo-separated into an effluent and paste. This effluent in turn is separated into Effluent I (Fraction I Effluent) and Faction I paste. The process can be repeated, for example, to obtain effluents and pastes for Fraction II+III, Fraction IV-1, Fraction IV-4, and Fraction V.

FIG. 2 depicts the design of a short-term treatment of previously 5-day differentiated C2C12 cells in 2% horse serum (HS), with a glucose utilization assay commencing twenty-four hours after treatment.

FIG. 3A reports the concentration of glucose remaining in the medium of C2C12 cells differentiated for 5 days to myotubes and subsequently treated for twenty-four hours with various treatment conditions, including: (1) untreated; (2) 1 mM Metformin (Met) positive control; (3) 0.5 mM Metformin; (4) 0.25 mM Metformin; (5) vehicle (10%); (6) PPF1 (5 mg/mL); (7) HAS1 (5 mg/mL); and (8) recombinant human albumin (rhAlbumin 5 mg/mL).

Figure 7:
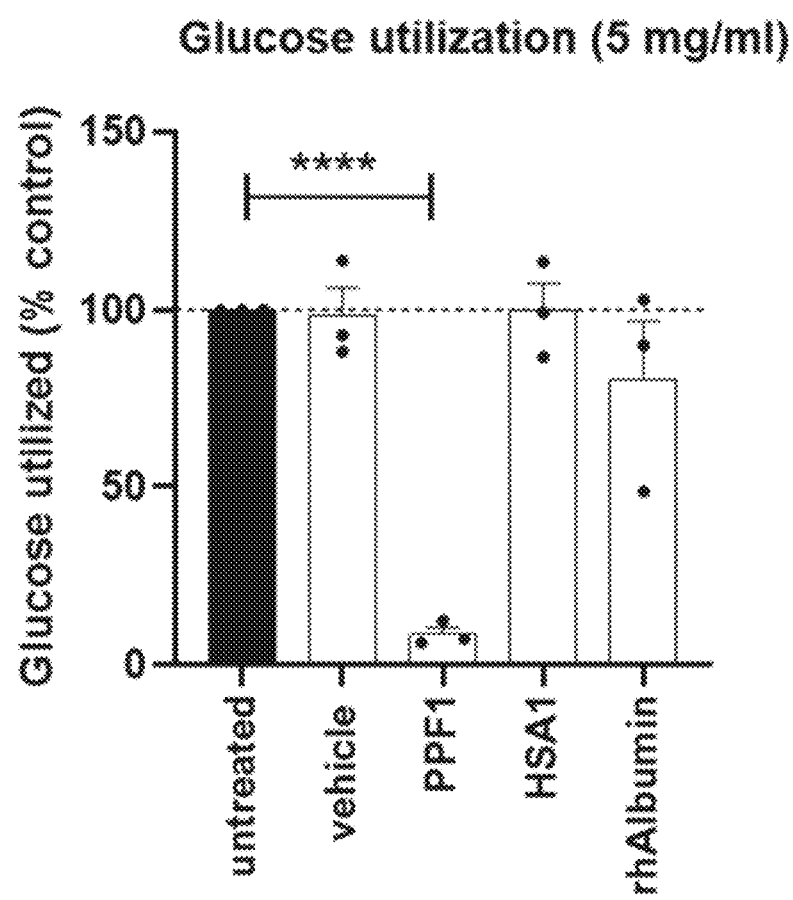

FIG. 7 reports glucose utilization remaining in the medium of C2C12 cells as per the experimental design depicted in FIG. 4 with 0% horse serum and treated as follows: untreated; vehicle; PPF1; HAS1; and rhAlbumin.

Figure 8:
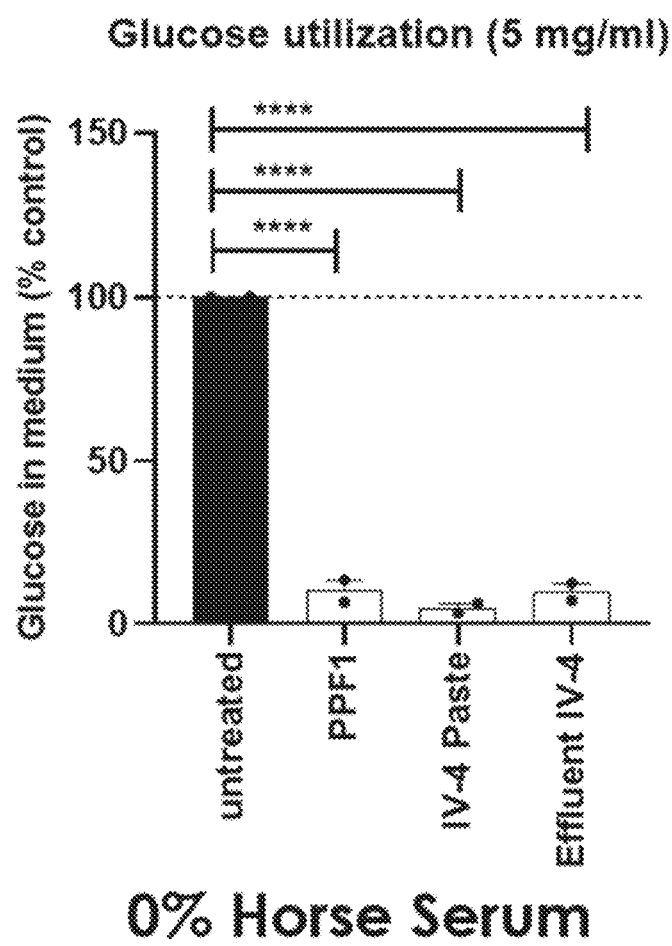

FIG. 8 reports glucose utilization in the medium of C2C12 cells as per the experimental design depicted in FIG. 4 with 0% horse serum and treated as follows: untreated; PPF1; Fraction IV-4 paste suspension and IV-4 Effluent.

Figure 9:
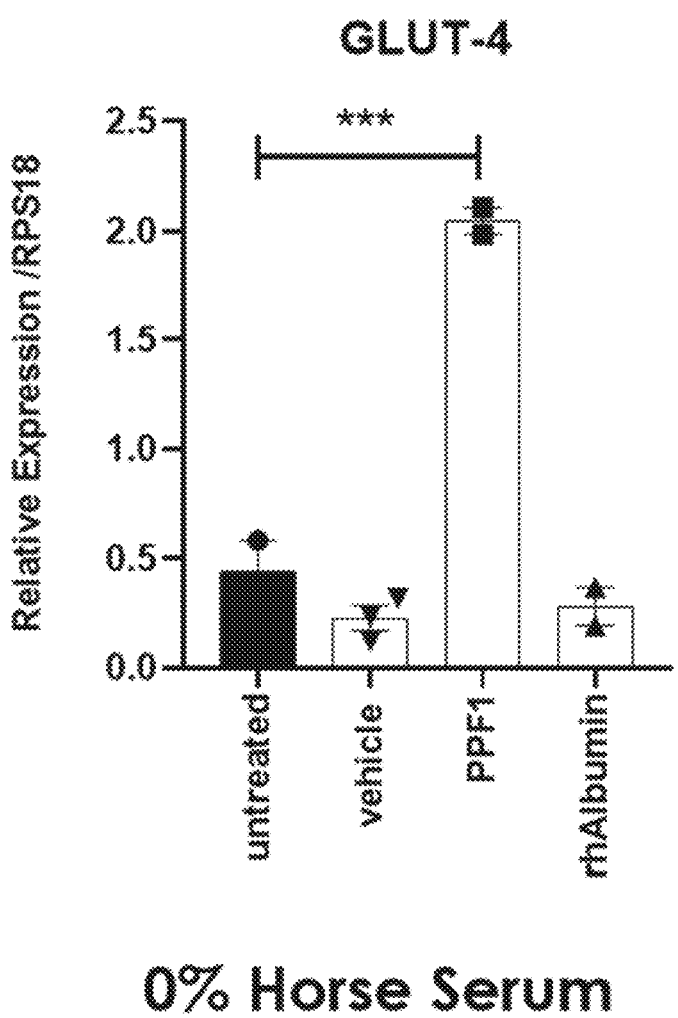

FIG. 9 reports the relative expression of glucose transporter type 4 (GLUT-4) in C2C12 myoblasts either untreated or treated with control vehicle, PPF1 (5 mg/mL), or recombinant human albumin (rhAlbumin 5 mg/mL).

Figure 10:
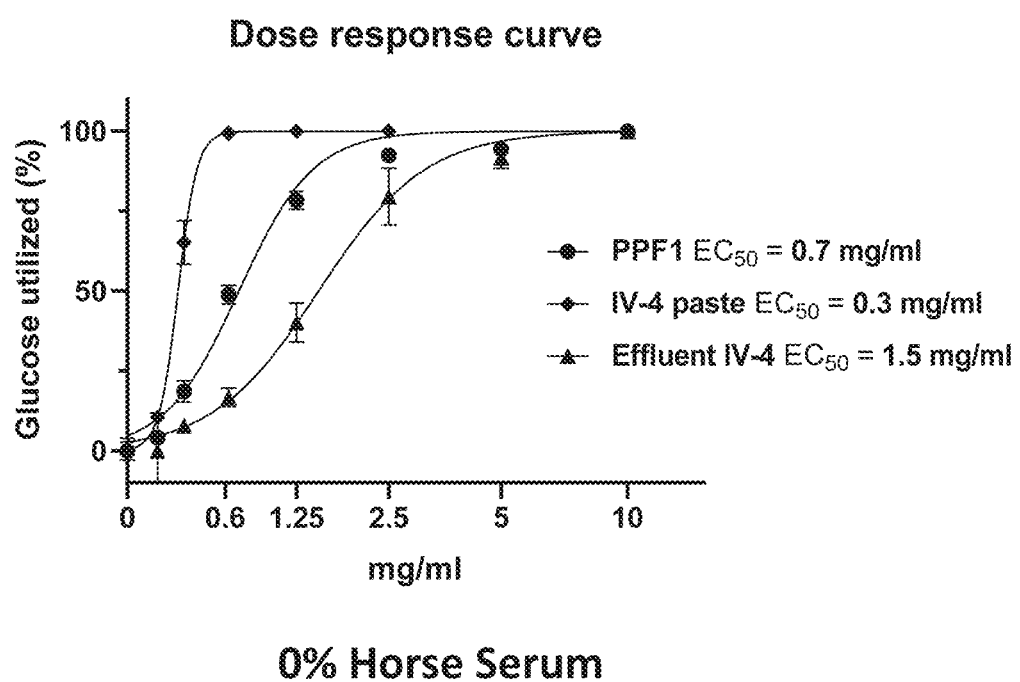

FIG. 10 reports the dose-response relationship between plasma fractions/fractionation products described in FIG. 8 and glucose utilization. Different treatment concentrations were added to cells (0.15, 0.3, 0.6, 1.25, 2.5, 5, and 10 mg/mL in the media). After 6 days of treatment and 48 hours with the same media, the amount of glucose left in the media was analyzed by the glucose utilization assay described previously above. All three compositions exhibited a dose-response relationship to glucose utilization.

FIG. 11A is a summary table of several experiments performed on C57BL/6 mice of various ages as well as young rats and tested for muscle weight values of the tibialis anterior, extensor digitorum longus, gastrocnemius, and soleus muscles. Each experiment also tested the effects of muscle weight on varying lengths of time after the last dose treatment with vehicle or PPF1.

Figure 11B:
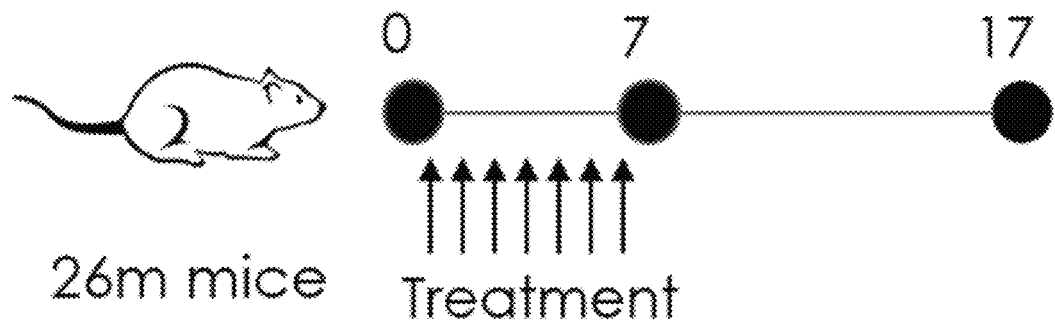

FIG. 11B is a representation of an experimental protocol to investigate muscle-related metrics on 22-month-old male C57B6 mice treated with PPF1 or control. Male C57B6 mice at 26 months of age were pulse dosed with PPF1 or control vehicle for 7 consecutive days (150 μL per dose, i.v.). Ten (10) days after the last dose, the following skeletal muscle groups were harvested: tibialis anterior (TA), extensor digitorum longus (EDL), and soleus (SOL). From each muscle group, the muscle to body weight (BW) ratio was obtained.

Figure 11C:
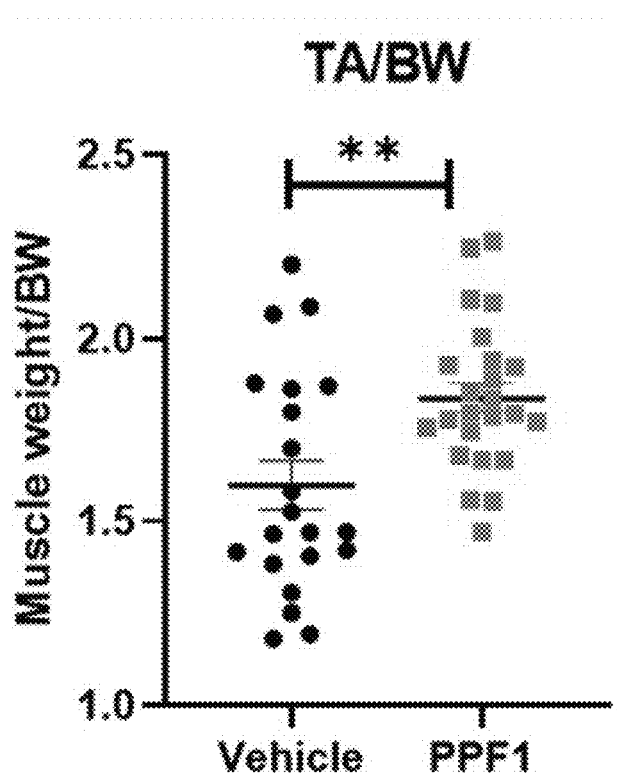

FIG. 11C shows that the tibialis anterior muscle tissue from the protocol of FIG. 11B significantly gained weight with PPF1 treatment compared to control (mean±SEM, **$p<0.01$ Welch's test).

Figure 11D:
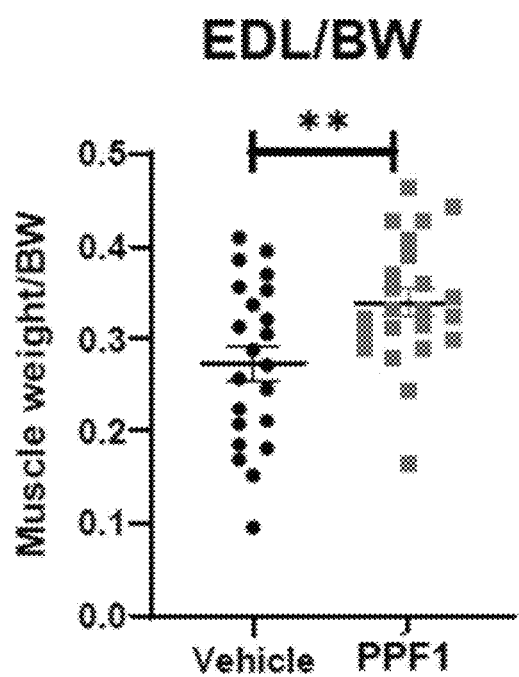

FIG. 11D shows that the extensor digitorum longus muscle tissue from the protocol of FIG. 11B significantly gained weight with PPF1 treatment compared to control (mean±SEM, **$p<0.01$ Welch's test).

Figure 11E:
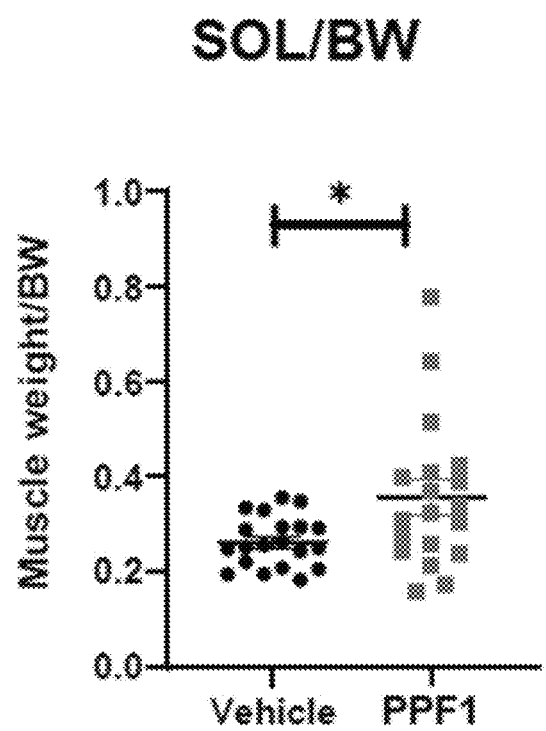

FIG. 11E shows that the soleus muscle tissue from the protocol of FIG. 11B significantly gained weight with PPF1 treatment compared to control (mean±SEM, *$p<0.05$ Welch's test).

Figure 12A:
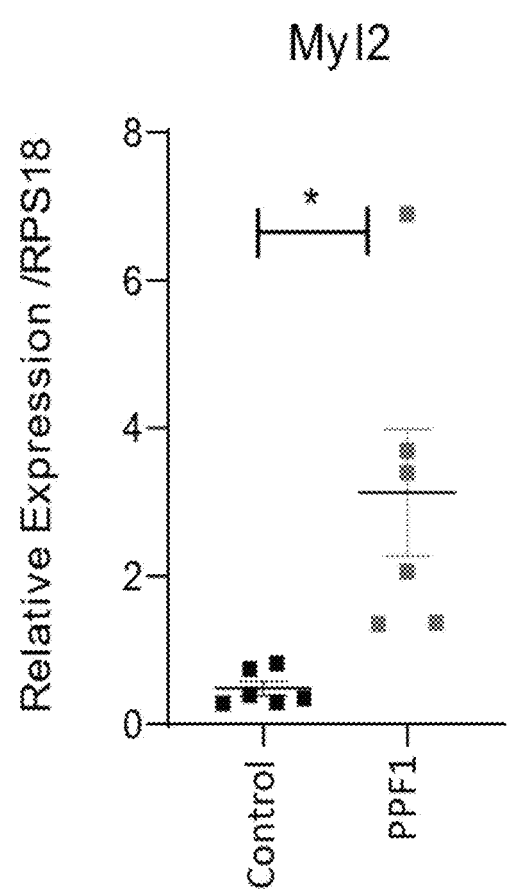

FIG. 12A shows the effect of PPF1 in inducing slow twitch fiber gene (Myl2) in the tibialis anterior muscle in mice.

Figure 12B:
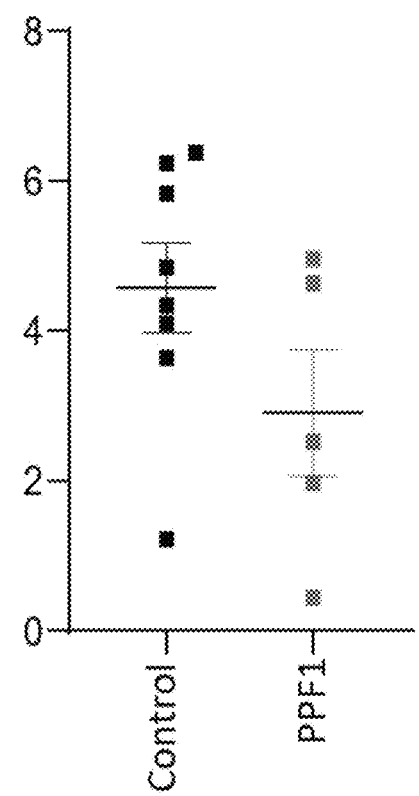
Figure 12C:
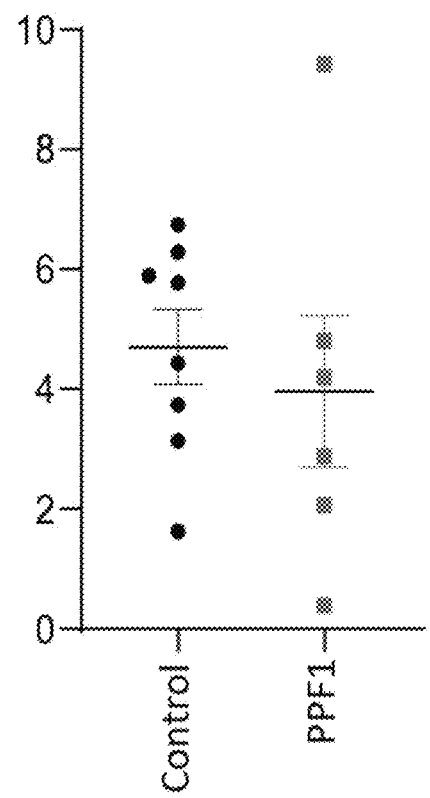
Figure 12D:
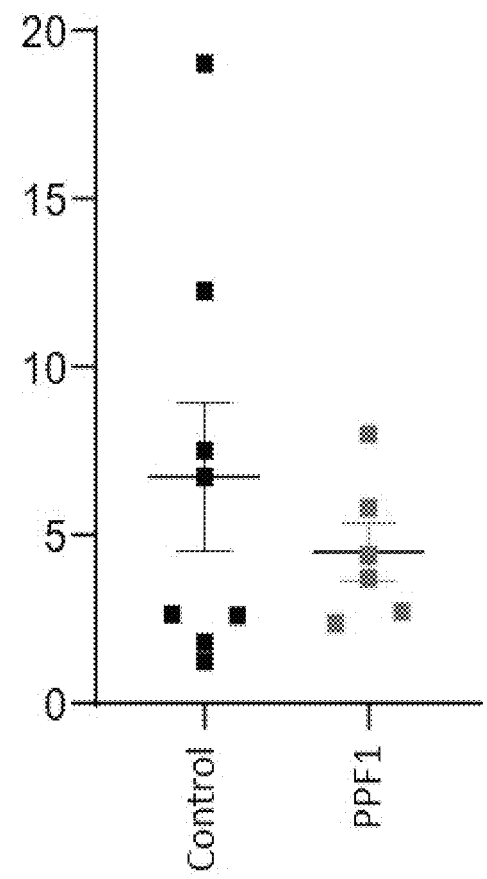

FIG. 12B, FIG. 12C, and FIG. 12D show the effects of PPF1 in decreasing expression in fast twitch fiber genes (Myh1(2x), Myh2(2a), and Myh4(2b)) respectively in the tibialis anterior muscle in mice.

FIG. 13A, FIG. 13B, FIG. 13C, and FIG. 13D all show C2C12 cells after 3 days of culture in 0% horse serum in conjunction with various treatment conditions.

Figure 13A:
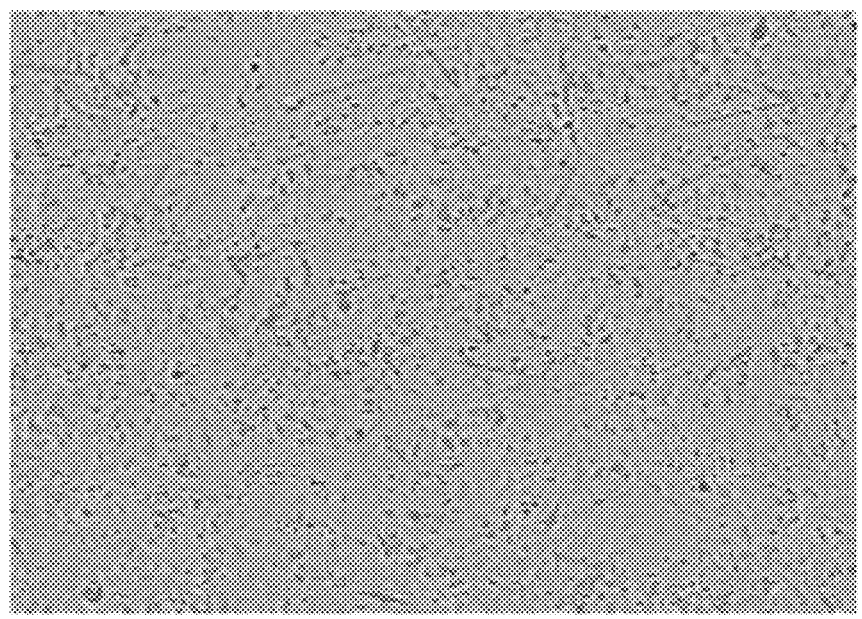

FIG. 13A shows the C2C12 cells in untreated conditions.

Figure 13B:
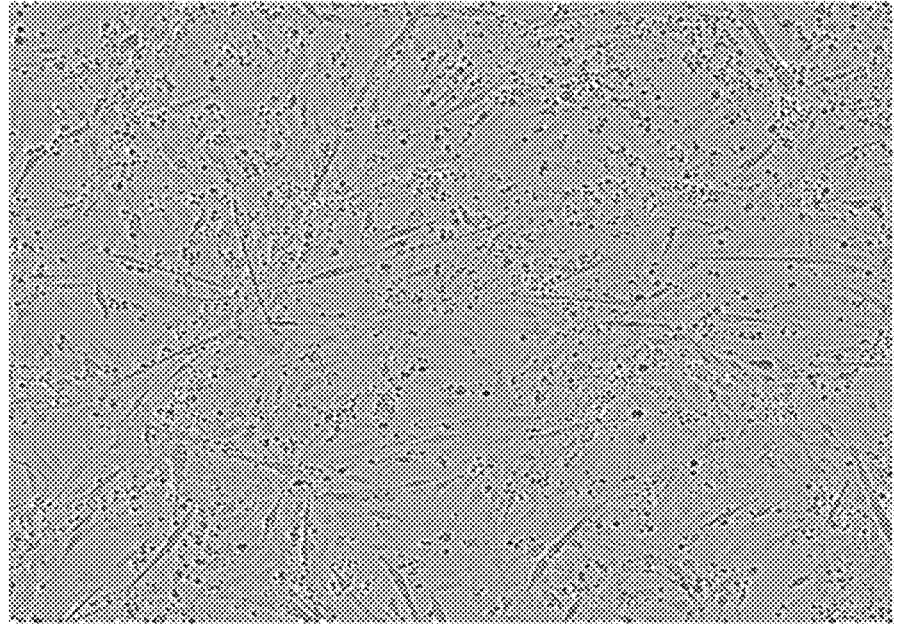

FIG. 13B shows C2C12 cells treated with 0.3% PPF1 for 3 days.

Figure 13C:
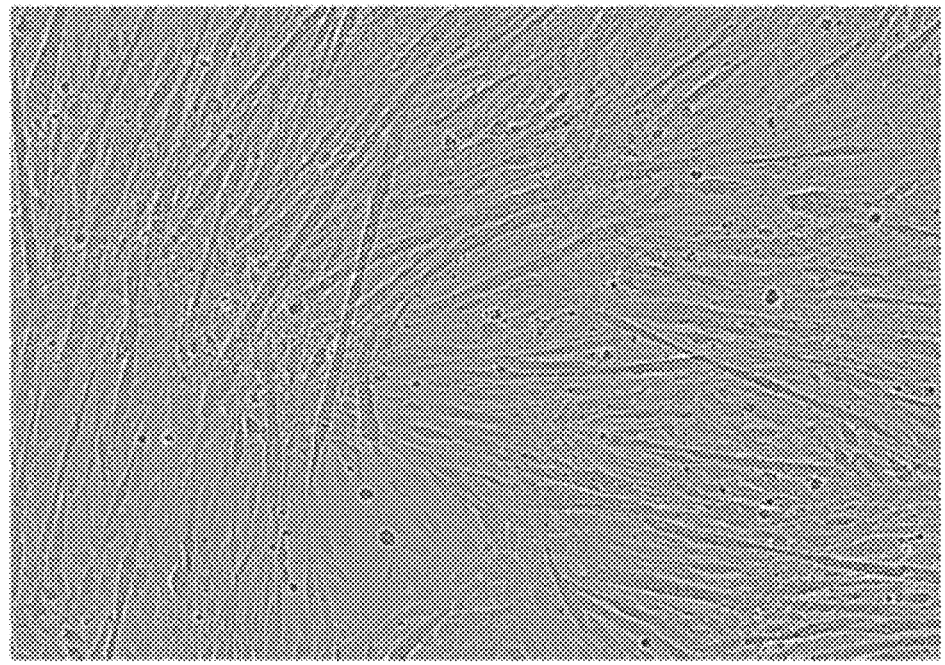
Figure 13D:
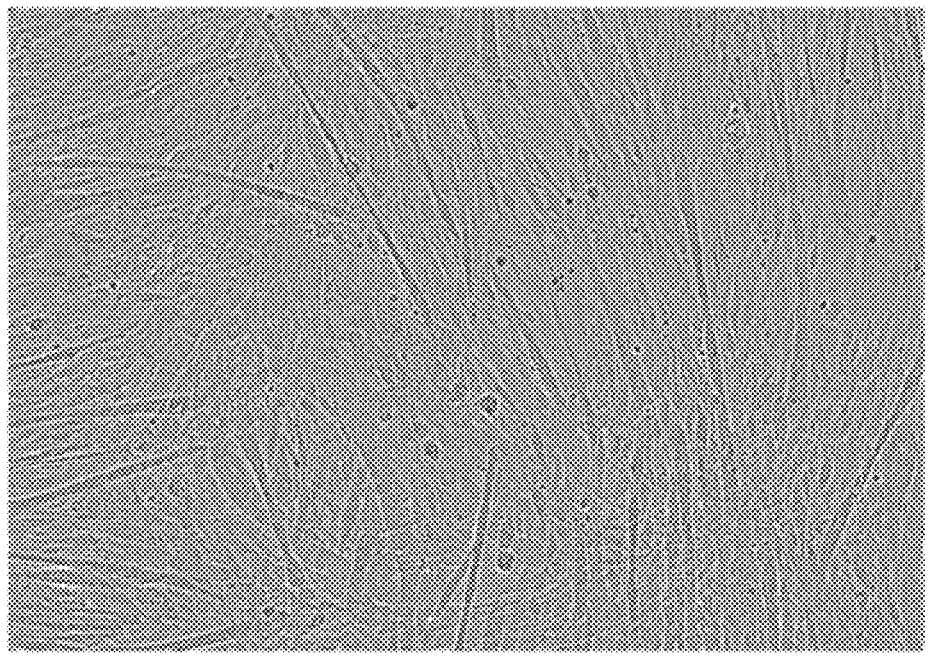

FIGS. 13C and 13D show C2C12 cells treated with 15 mg/mL fraction IV-1 paste suspension and 0.6 mg/mL IV-1 paste suspension respectively for 3 days.

Figure 14:
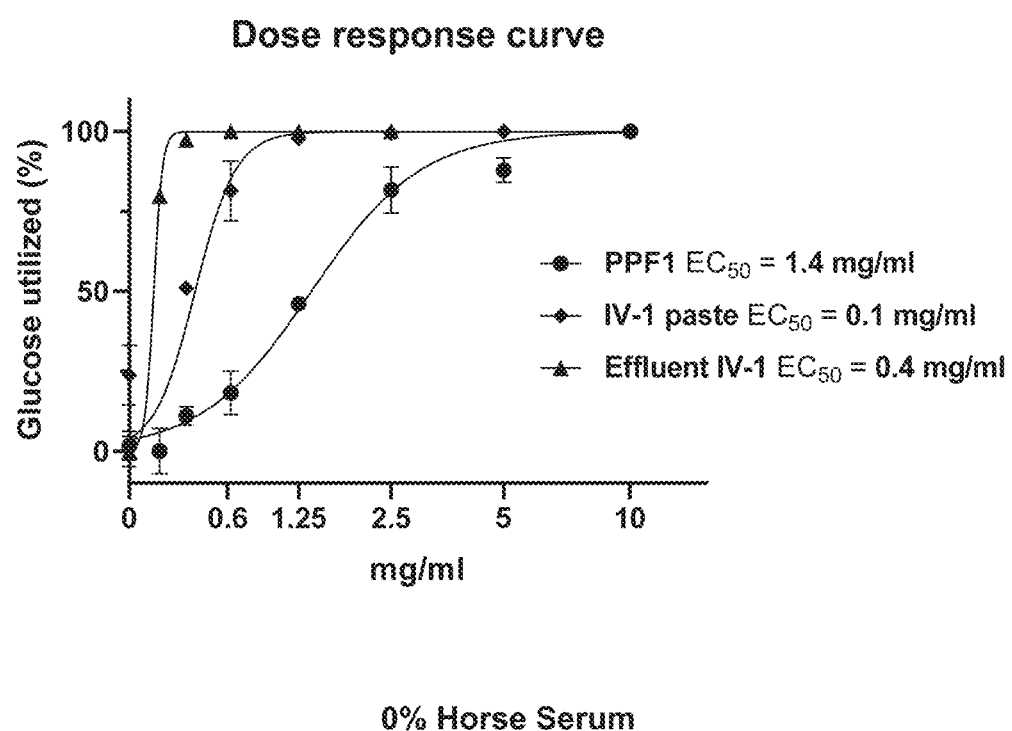

FIG. 14 reports the dose-response relationship between plasma fractions/fractionation products by normalized glucose utilized (%), from C2C12 supernatant, 24 hours after the last media change. In total, the cells were cultures in 0% horse serum for six days. The graph depicts the effect on glucose utilization by increasing doses of PPF1, fraction IV-1 paste suspension, and fraction IV-1 effluent.

Figure 15:
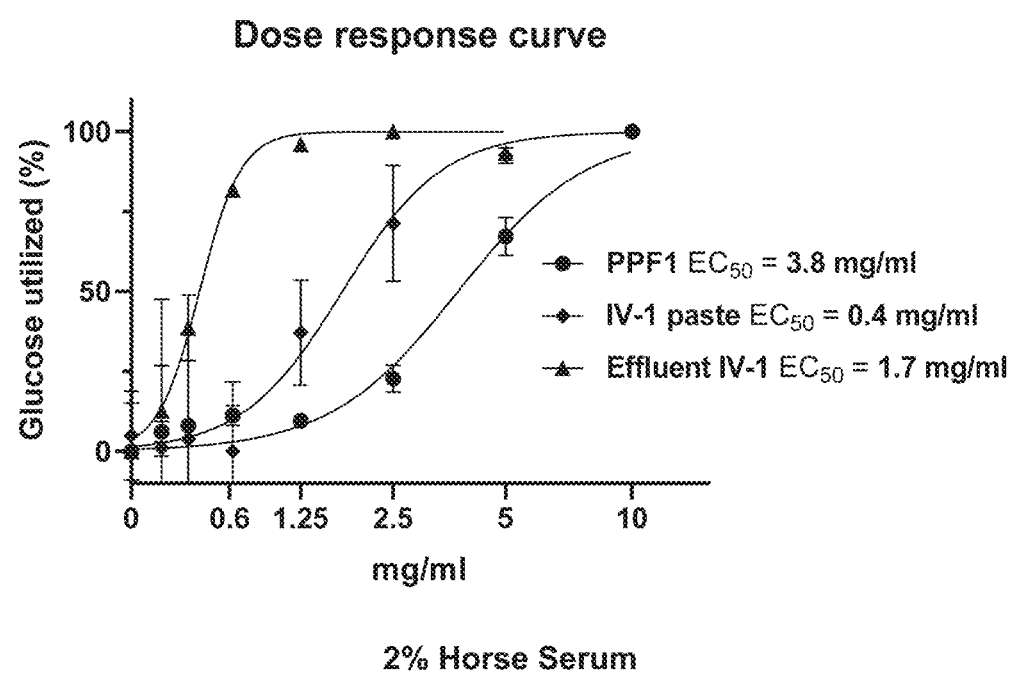

FIG. 15 reports the dose-response relationship between plasma fractions/fractionation products by normalized glucose utilized (%), from C2C12 supernatant, 24 hours after the last media change. In total cells were cultured in 2% horse serum for six days. The graph depicts the effect on glucose utilization by increasing doses of PPF1, fraction IV-1 paste suspension, and fraction IV-1 effluent.

Figure 16A:
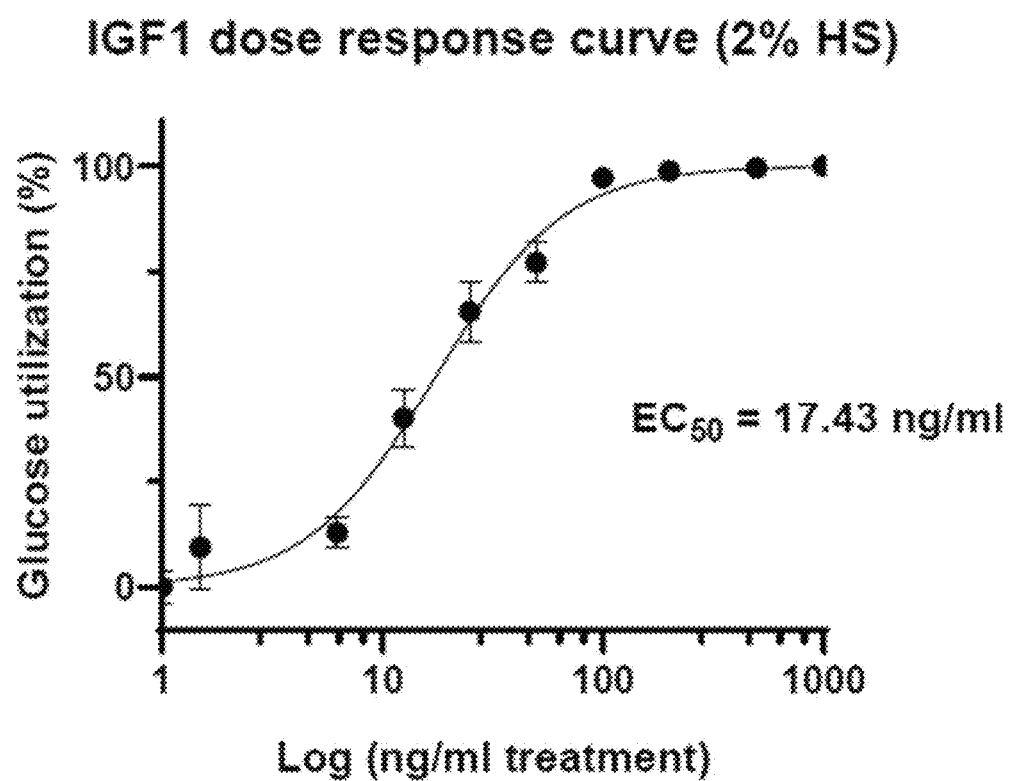
Figure 16B:
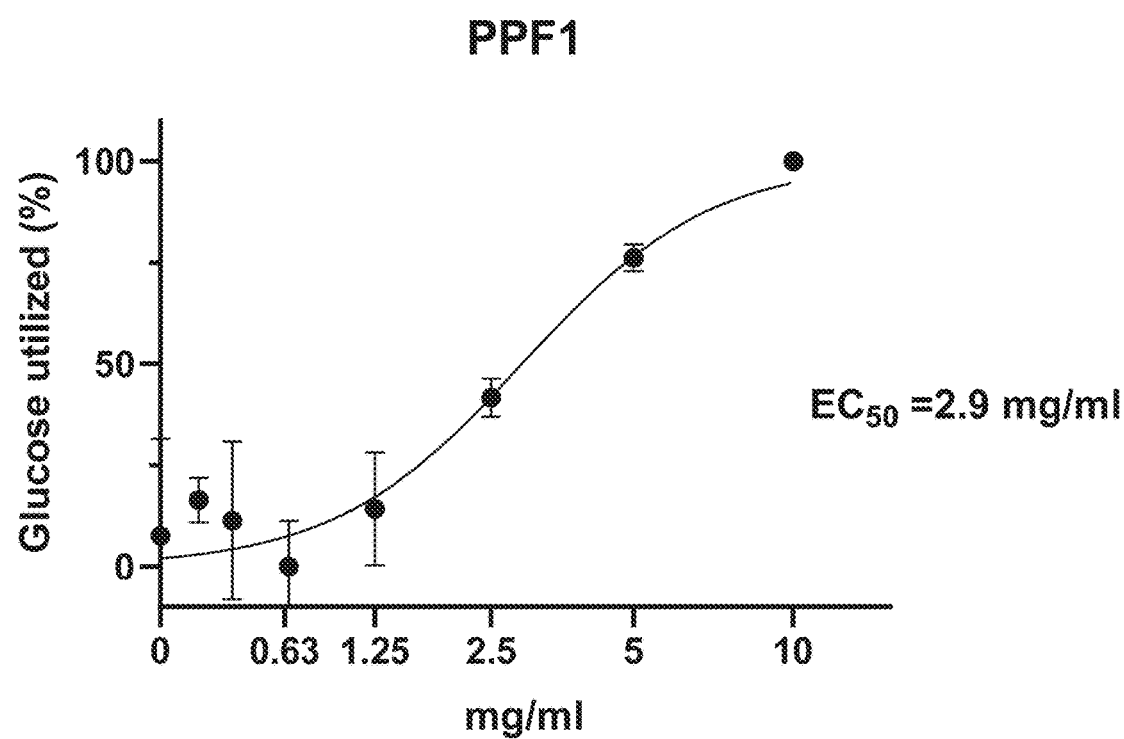

FIG. 16A and FIG. 16B report the effects of insulin-like growth factor-1 (IGF-1) on glucose utilization in C2C12 cells treated in 2% horse serum.

FIG. 16A reports the dose-response relationship between IGF-1 treatment (x-axis) and glucose utilization, revealing an $EC_{50}$ of 17.43 ng/mL.

FIG. 16B reports the dose-response relationship between PPF1 treatment and glucose utilization, revealing an $EC_{50}$ of 2.9 mg/mL containing 0.87 ng/mL IGF1.

Figure 17A:
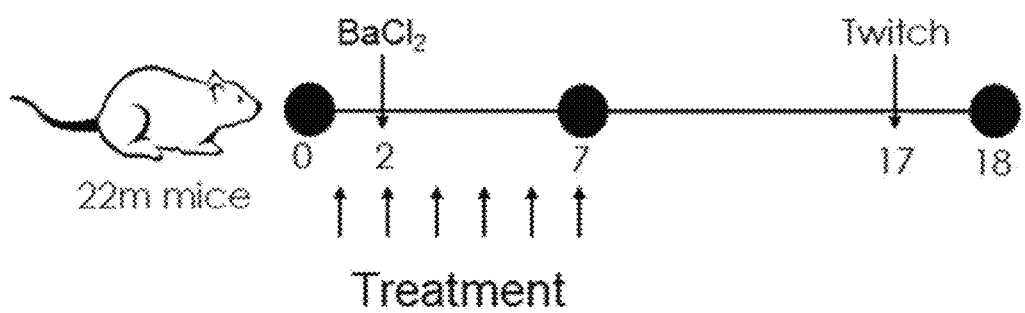

FIG. 17A is a representation of an experimental protocol to investigate muscle recovery using different fraction treatments on a barium chloride induced injury model.

Figure 17B:
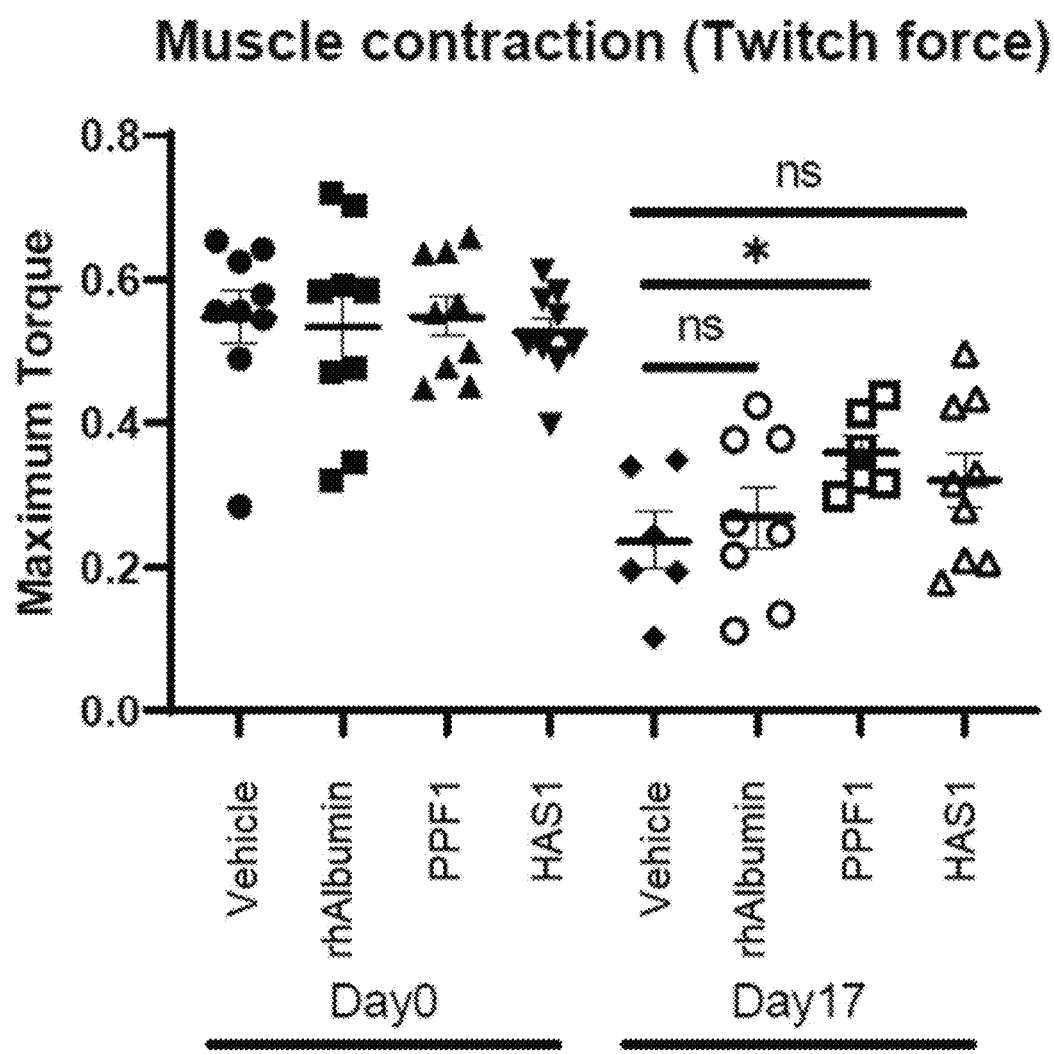

FIG. 17B reports the results of twitch force measurements taken a day 0 and day 17 of the protocol described in FIG. 17A where treatment included vehicle, recombinant human albumin, PPF1, or HAS1.

Figure 18A:
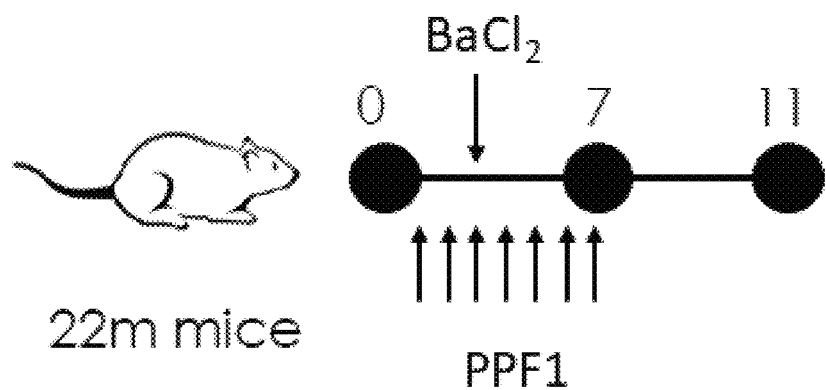

FIG. 18A is a representation of an experimental protocol to investigate the effects of plasma fractions on serum mouse IGF1 levels.

Figure 18B:
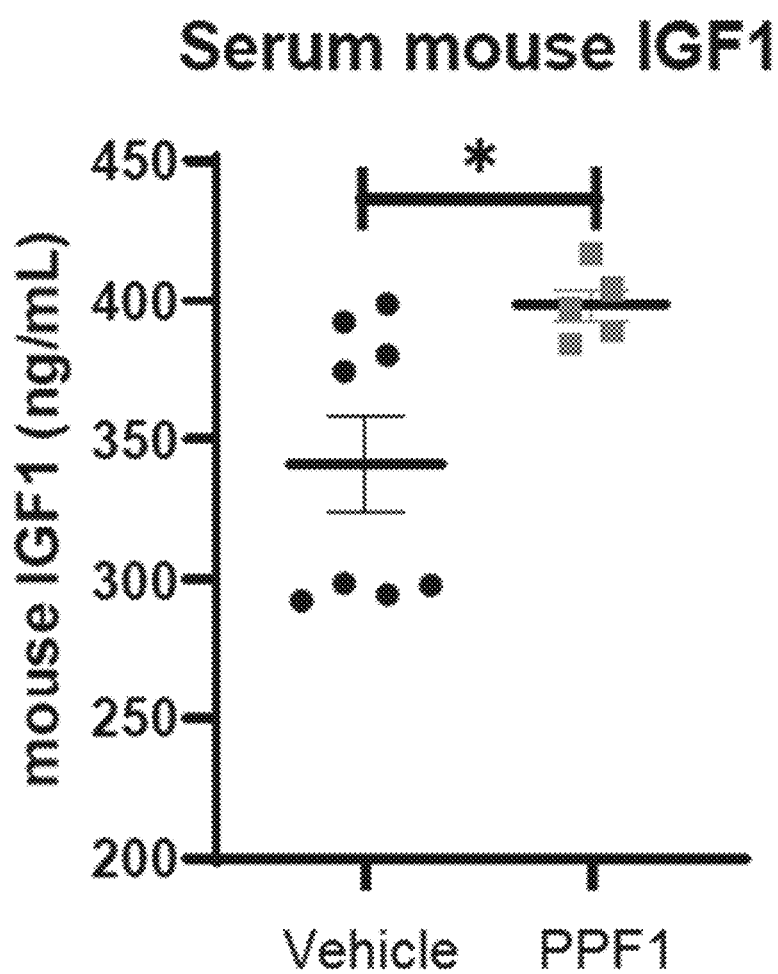

FIG. 18B reveals that PPF1 treatment, even 10 days after the last dose as described in the protocol from FIG. 18A, is associated with significantly increased mouse IGF-1 in the serum.

Figure 19A:
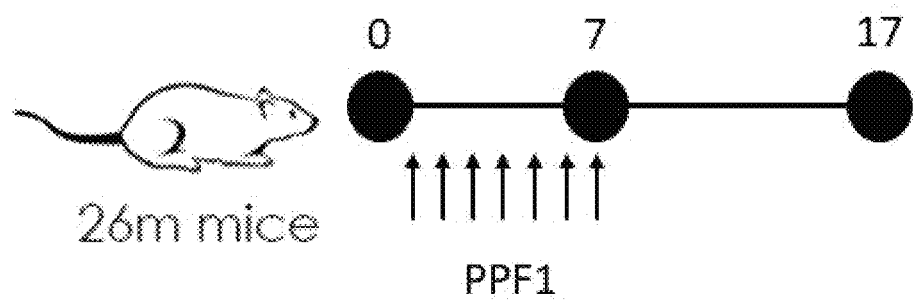

FIG. 19A is a representation of an experimental protocol to investigate whether plasma fractions can decrease heart weight in aged C57BL/6 mice, in a model of hypertrophic cardiac muscle observed in aged mammals.

Figure 19B:
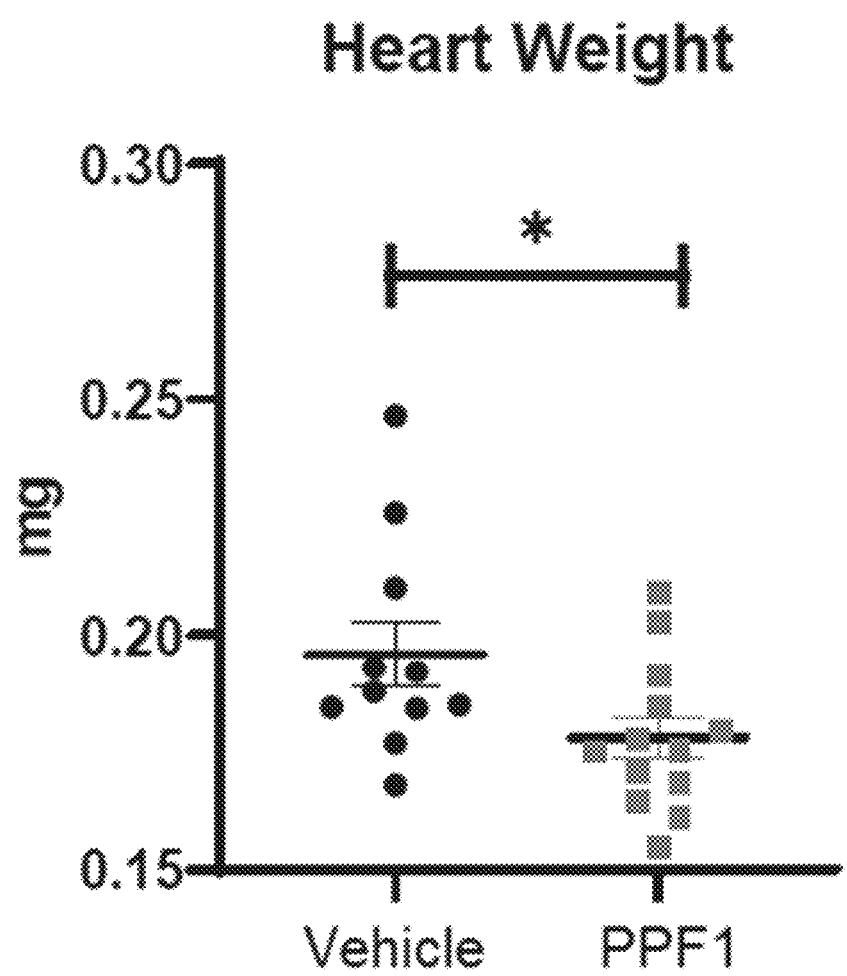

FIG. 19B shows heart weight in milligrams for both vehicle and PPF1 treated mice.

Figure 19C:
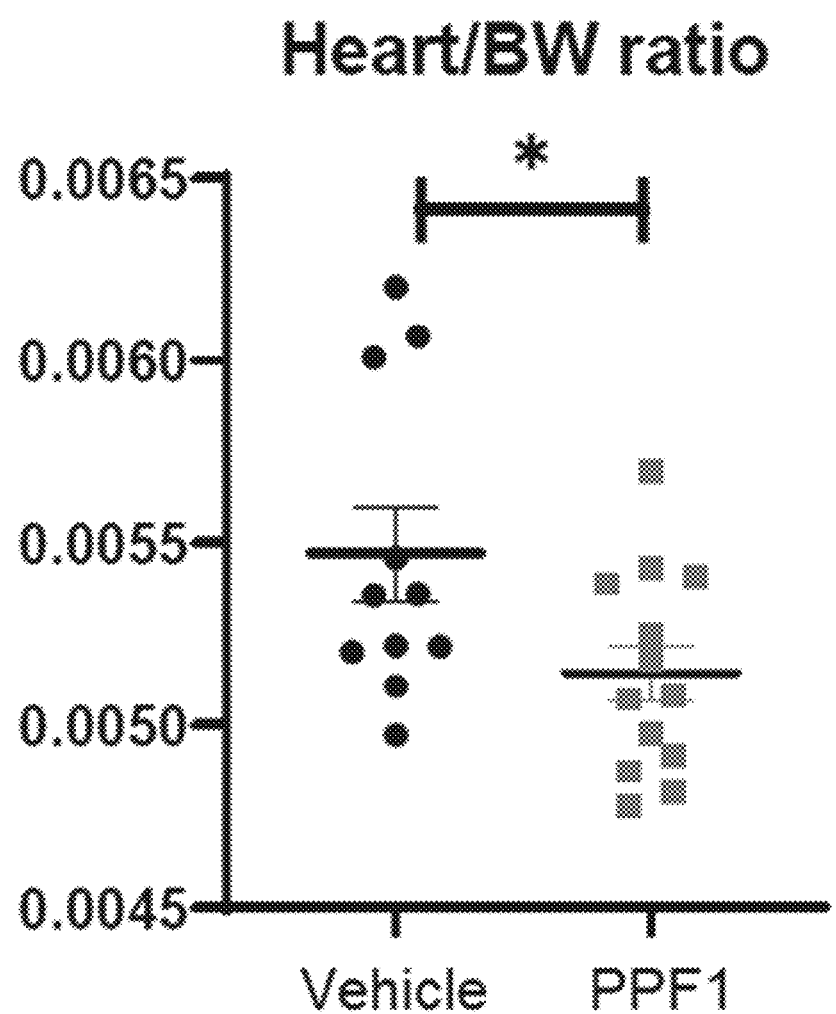

FIG. 19C shows the heart weight to body weight ratios of the same mice described in FIG. 19B.

Figure 20A:
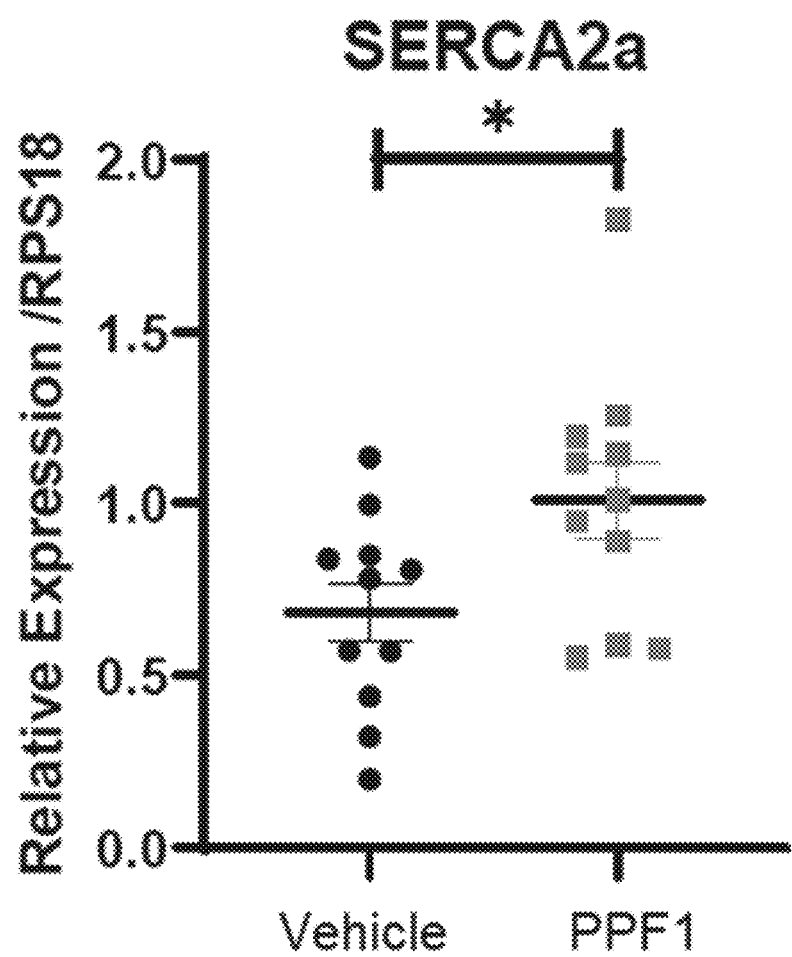
Figure 20B:
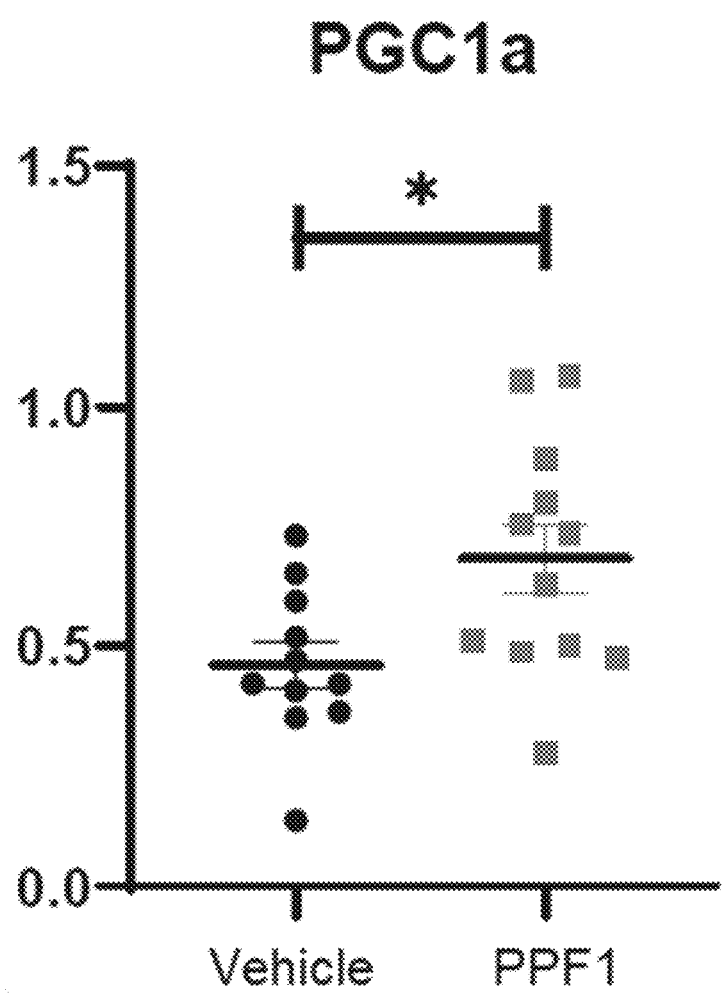
Figure 20C:
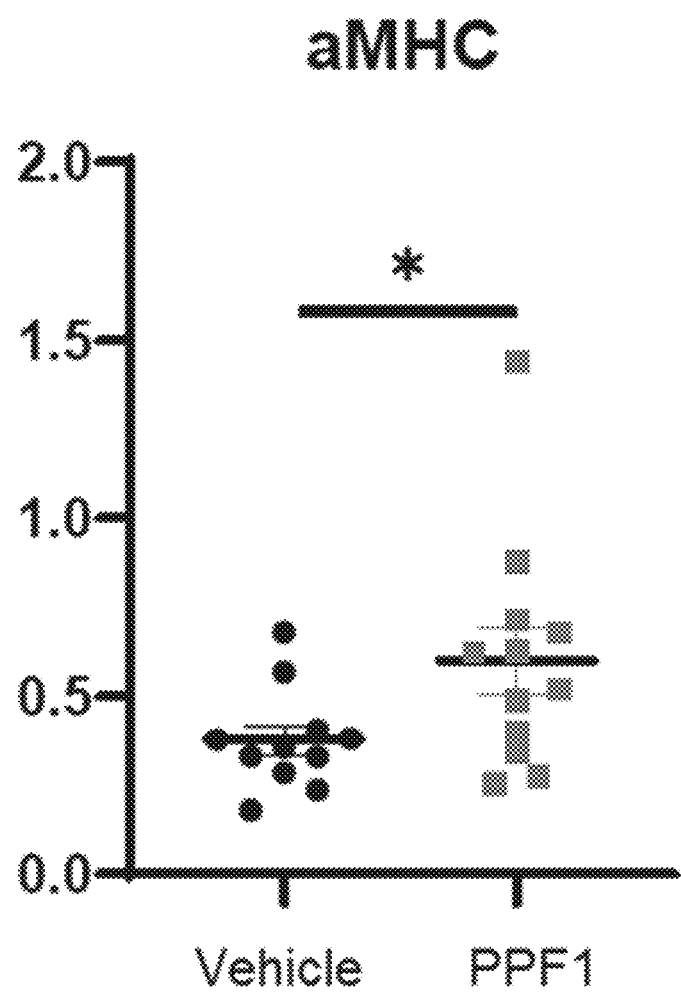

FIG. 20A, FIG. 20B, and FIG. 20C report expression of cardio-protective marker RNA levels in the hearts described in FIGS. 19A, 19B, and 19C.

FIG. 20A shows that RNA expression of sarco-endoplasmic reticulum calcium-ATPase (SERCA2a) significantly increases with PPF1 treatment compared to control.

FIG. 20B shows that RNA expression of peroxisome proliferator activated receptor gamma coactivator 1 alpha (PGC1a) significantly increases with PPF1 treatment compared to control.

FIG. 20C shows that RNA expression of α-myosin heavy chain (aMHC) significantly increases with PPF1 treatment compared to control.

Figure 21A:
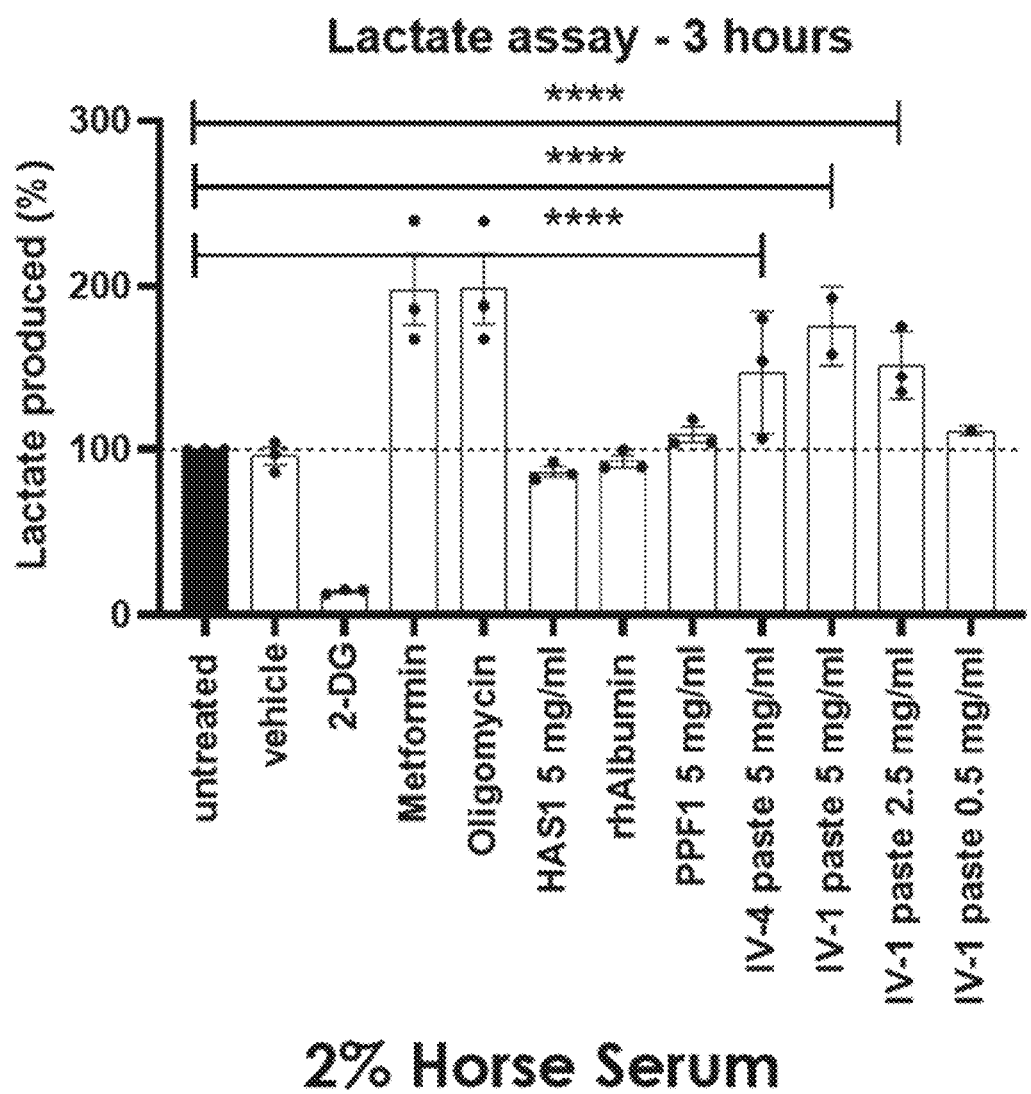

FIG. 21A shows the amount of lactate (a myogenic differentiating factor) produced in C2C12 cells in response to three (3) hours of treatment with various factors. These included vehicle, 2-DG (negative control), metformin (positive control), oligomycin, HAS1, recombinant human albumin (rhAlbumin), PPF1, fraction IV-1 paste suspension, and three different concentrations of fraction IV-1 paste suspension.

Figure 21B:
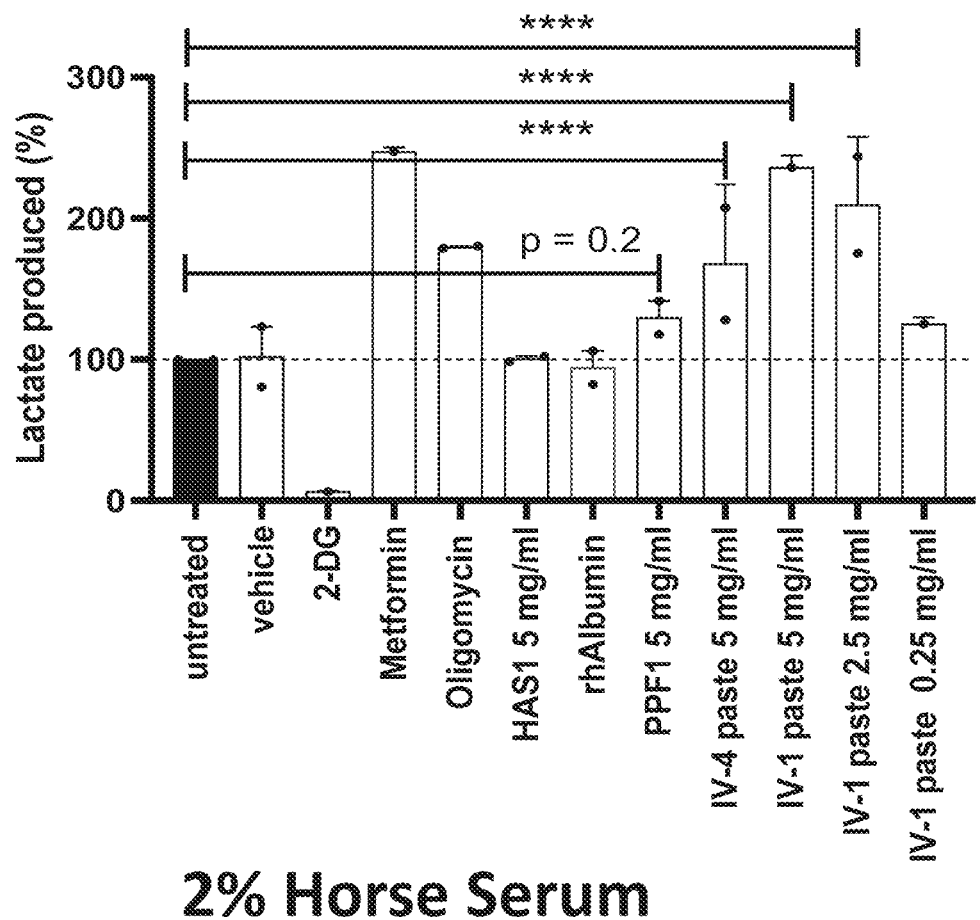

FIG. 21B shows the effects on lactate production on C2C12 cells after five (5) hours of treatment with the various factors described in FIG. 21A.

VI. DETAILED DESCRIPTION OF THE INVENTION

A. Introduction

The present invention relates to the treatment of disorders or diseases of muscle, including skeletal muscle. Plasma fractions including products of blood plasma fractionation are shown to have marked activity in muscle regenerative processes such as an increased utilization of glucose by myoblast cells, increased differentiation from myoblast to myotube formation, increased contractility, and induction of slow twitch fiber-associated genes. Plasma fractions present several advantages over whole plasma serum since the blood plasma fractionation process can remove problematic coagulation factors as well as obviate the need for blood cross-matching. Additionally, plasma fractions have exhibited unexpected improvement in efficacy compared to young plasma in certain analyses (see, e.g., U.S. patent application Ser. No. 15/499,694 and U.S. patent application Ser. No. 16/432,114; and which are both incorporated by reference herein in their entirety). Thus, predicting efficacy from whole plasma serum to products of plasma fractionation is not subject to reasonable predictability.

Before describing the present invention in detail, it is to be understood that this invention is not limited to a particular method or composition described, as such may, of course, vary. It is also understood that the terminology used herein is for the purpose of describing particular embodiments only, and is not intended to be limiting, since the scope of the present invention will be limited only by the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein have discrete components and features which may be readily separated from or combined with the features of any of the other several embodiments without departing from the scope or the spirit of the present invention. Any recited method can be carried out in the order of events recited or in any other order which is logically possible.

B. Definitions

Unless otherwise defined, all technical and scientific terms used herein have the same meaning as commonly understood by one having ordinary skill in the art to which the invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those having skill in the art, and so forth.

In describing methods of the present invention, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As such, subjects of the invention, include but are not limited to mammals, e.g., humans and other primates, such as chimpanzees and other apes and monkey species; and the like, where in certain embodiments the subject are humans. The term subject is also meant to include a person or organism of any age, budget or other physical characteristic, where the subjects may be an adult, a child, an infant or a newborn.

By a "young" or "young individual" it is meant an individual that is of chronological age of 40 years old or younger, e.g., 35 years old or younger, including 30 years old or younger, e.g., 25 years old or younger or 22 years old or younger. In some instances, the individual that serves as the source of the young plasma-comprising blood product is one that is 10 years old or younger, e.g., 5 years old or younger, including 1-year-old or younger. In some instances, the subject is a newborn and the source of the plasma product is the umbilical cord, where the plasma product is harvested from the umbilical cord of the newborn. As such, "young" and "young individual" may refer to a subject that is between the ages of 0 and 40, e.g., 0, 1, 5, 10, 15, 20, 25, 30, 35, or 40 years old. In other instances, "young" and "young individual" may refer to a biological (as opposed to chronological) age such as an individual who has not exhibited the levels of inflammatory cytokines in the plasma exhibited in comparatively older individuals. Conversely, these "young" and "young individual" may refer to a biological (as opposed to chronological) age such as an individual who exhibits greater levels of anti-inflammatory cytokines in the plasma compared to levels in comparatively older individuals. By way of example, and not limitation, the inflammatory cytokine is Eotaxin, and the fold difference between a young subject or young individual and older individuals is at least 1.5-fold. Similarly, the fold difference between older and younger individuals in other inflammatory cytokines may be used to refer to a biological age. (See U.S. patent application Ser. No. 13/575,437 which is herein incorporated by reference). Usually, the individual is healthy, e.g., the individual has no hematological malignancy or autoimmune disease at the time of harvest.

As used herein, "treatment" refers to any of (i) the prevention of the disease or disorder, or (ii) the reduction or elimination of symptoms of the disease or disorder. Treatment may be effected prophylactically (prior to the onset of disease) or therapeutically (following the onset of the disease). The effect may be prophylactic in terms of completely or partially preventing a disease or symptom thereof and/or may be therapeutic in terms of a partial or complete cure for a disease and/or adverse effect attributable to the disease. Thus, the term "treatment" as used herein covers any treatment of a condition associated with a muscle injury, muscle disease, muscle disorder, or muscle condition that could benefit from improved muscle generation, regeneration, healing, function, or restoration in a mammal, and includes: (a) preventing the condition from occurring in a subject; (b) inhibiting the condition, i.e., arresting its occurrence; or (c) relieving the condition, i.e., causing regression of the condition. Treatment may result in a variety of different physical manifestations, e.g., modulation in gene expression, rejuvenation of tissue or organs, decreasing inflammation, etc. The therapeutic agent may be administered before, during or after the onset of the condition. The subject therapy may be administered during the symptomatic stage of the condition, and in some cases after the symptomatic stage of the condition.

Blood Products Comprising Plasma Components. In practicing the subject methods, a blood product comprising plasma components is administered to an individual in need thereof, e.g., an individual suffering from one or more of the following conditions: a muscle injury, muscle disease, muscle disorder, or muscle condition that could benefit from improved muscle generation, regeneration, healing, function, or restoration. As such, methods according to embodiments of the invention include administering a blood product comprising plasma components from an individual (the "donor individual", or "donor") to an individual suffering from one or more of the following conditions: a muscle injury, muscle disease, muscle disorder, or muscle condition that could benefit from improved muscle generation, regeneration, healing, function, or restoration (the "recipient individual" or "recipient"). By a "blood product comprising plasma components," it is meant any product derived from blood that comprises plasma (e.g. whole blood, blood plasma, or fractions thereof). The term "plasma" is used in its conventional sense to refer to the straw-colored/pale-yellow liquid component of blood composed of about 92% water, 7% proteins such as albumin, gamma globulin, anti-hemophilic factor, and other clotting factors, and 1% mineral salts, sugars, fats, hormones and vitamins. Non-limiting examples of plasma-comprising blood products suitable for use in the subject methods include whole blood treated with anti-coagulant (e.g., EDTA, citrate, oxalate, heparin, etc.), blood products produced by filtering whole blood to remove white blood cells ("leukoreduction"), blood products consisting of plasmapheretically-derived or apheretically-derived plasma, fresh-frozen plasma, blood products consisting essentially of purified plasma, and blood products consisting essentially of plasma fractions. In some instances, plasma product that is employed is a non-whole blood plasma product, by which is meant that the product is not whole blood, such that it lacks one or more components found in whole blood, such as erythrocytes, leukocytes, etc., at least to the extent that these components are present in whole blood. In some instances, the plasma product is substantially, if not completely, acellular, where in such instances the cellular content may be 5% by volume or less, such as 1% or less, including 0.5% or less, where in some instances acellular plasma fractions are those compositions that completely lack cells, i.e., they include no cells.

Collection of blood products comprising plasma components. Embodiments of the methods described herein include administration of blood products comprising plasma components which can be derived from donors, including human volunteers. The term, "human-derived" can refer to such products. Methods of collection of plasma comprising blood products from donors are well-known in the art. (See, e.g., AABB TECHNICAL MANUAL, (Mark A. Fung, et al., eds., 18th ed. 2014), herein incorporated by reference).

In one embodiment, donations are obtained by venipuncture. In another embodiment, the venipuncture is only a single venipuncture. In another embodiment, no saline volume replacement is employed. In a preferred embodiment, the process of plasmapheresis is used to obtain the plasma comprising blood products. Plasmapheresis can comprise the removal of a weight-adjusted volume of plasma with the return of cellular components to the donor. In the preferred embodiment, sodium citrate is used during plasmapheresis in order to prevent cell clotting. The volume of plasma collected from a donor is preferably between 690 to 880 mL after citrate administration, and preferably coordinates with the donor's weight.

C. Plasma Fractions

During the Second World War, there arose a need for a stable plasma expander which could be employed in the battlefield when soldiers lost large amounts of blood. As a result, methods of preparing freeze-dried plasma were developed. However, use of freeze-dried plasma was difficult in combat situations since reconstitution required sterile water. As an alternative, Dr. E. J. Cohn suggested that albumin could be used, and prepared a ready-to-use stable solution that could be introduced immediately for treatment of shock. (See Johan, Current Approaches to the Preparation of Plasma Fractions in (Biotechnology of Blood) 165 (Jack Goldstein ed., 1st ed. 1991)). Dr. Cohn's procedure of purifying plasma fractions utilized cold ethanol for its denaturing effect and employs changes in pH and temperature to achieve separation.

An embodiment of the methods described herein includes the administration of plasma fractions to a subject. Fractionation is the process by which certain protein subsets are separated from plasma. Fractionation technology is known in the art and relies on steps developed by Cohn et al. during the 1940s. (E. Cohn, Preparation and properties of serum and plasma proteins. IV. A system for the separation into fractions of the protein and lipoprotein components of biological tissues and fluids. 68 J Am Chem Soc 459 (1946), herein incorporated by reference). Several steps are involved in this process, each step involving specific ethanol concentrations as well as pH, temperature, and osmolality shifts which result in selective protein precipitation. Precipitates are also separated via centrifugation or precipitation. The original "Cohn fractionation process" involved separation of proteins through precipitates into five fractions, designated fraction I, fraction II+III, fraction IV-1, fraction IV-4 and fraction V. Albumin was the originally identified endpoint (fraction V) product of this process. In accordance with embodiments of the invention, each fraction, filtrate (or effluent or sometimes referred to as waste streams from a prior separation step) contains or potentially contains therapeutically useful protein fractions. (See Thierry Burnouf, Modern Plasma Fractionation, 21(2) Transfusion Medicine Reviews 101 (2007); Adil Denizli, Plasma fractionation: conventional and chromatographic methods for albumin purification, 4 J. Biol. & Chem. 315, (2011); Gjessing E C, et al., J. Biol. & Chem. (174):682-96 (1948); and T. Brodniewicz-Proba, Human Plasma Fractionation and the Impact of New Technologies on the Use and Quality of Plasma-derived Products, 5 Blood Reviews 245 (1991), and U.S. Pat. Nos. 3,869,431, 5,110,907, 5,219,995, 7,531,513, and 8,772,461 which are herein incorporated by reference). Adjustment of the above experimental parameters can be made in order to obtain specific protein fractions.

More recently, fractionation has reached further complexity, and as such, comprises additional embodiments of the invention. This recent increase in complexity has occurred through: the introduction of chromatography resulting in isolation of new proteins from existing fractions like cryoprecipitate, cryo-poor plasma, and Cohn fractions; increasing IgG recovery by integrating chromatography and the ethanol fractionation process; and viral reduction/inactivation/removal. (Id.) In order to capture proteins at physiological pH and ionic strength, anion-exchange chromatography can be utilized. This preserves functional activity of proteins and/or protein fractions. Heparin and monoclonal antibodies are also used in affinity chromatography. Additionally, fractionation using gel filtration, fraction by salt, and fractionation by polyethylene glycol are used. (Hosseini M Iran J Biotech, 14(4): 213-20 (2016) herein incorporated by reference). One of ordinary skill in the art would recognize that the parameters and techniques described above may be adjusted to obtain specifically desired plasma protein-containing fractions.

Blood plasma fractionation can also be ammonium sulfate-based. (See, e.g., Odunuga O O, *Biochem Compounds*, 1:3 (2013); Wingfield P T, *Curr Protoc Protein Sci, Appx.* 3 (2001), herein incorporated by reference). In addition to obtaining specific blood fractions, ammonium sulfate-based fractionation has been employed to reduce abundant proteins from plasma. (Saha S, et al., *J. Proteomics Bioinform,* 5(8) (2012), herein incorporated by reference).

In an embodiment of the invention, blood plasma is fractionated in an industrial setting. Frozen plasma is thawed at 1° C. to 4° C. Continuous refrigerated centrifugation is applied to the thawed plasma and cryoprecipitate isolated. Recovered cryoprecipitate is frozen at −30° C. or lower and stored. The cryoprecipitate-poor ("cryo-poor") plasma is immediately processed for capture (via, for example, primary chromatography) of labile coagulation factors such as factor IX complex and its components as well as protease inhibitors such as antithrombin and C1 esterase inhibitor. Serial centrifugation and precipitate isolation can be applied in subsequent steps. Such techniques are known to one of ordinary skill in the art and are described, for example, in U.S. Pat. Nos. 4,624,780, 5,219,995, 5,288,853, and U.S. patent application nos. 20140343255 and 20150343025, which disclosures are incorporated by reference in their entirety herein.

In an embodiment of the invention, the plasma fraction may comprise a plasma fraction containing a substantial concentration of albumin. In another embodiment of the invention, the plasma fraction may comprise a plasma fraction containing a substantial concentration of IgG or intravenous immune globulin (IGIV) (e.g. Gamunex-C®). In another embodiment of the invention the plasma fraction may comprise an IGIV plasma fraction, such as Gamunex-C® which has been substantially depleted of immune globulin (IgG) by methods well-known by one of ordinary skill in the art, such as for example, Protein A-mediated depletion. (See Keshishian, H., et al., Multiplexed, Quantitative Workflow for Sensitive Biomarker Discovery in Plasma Yields Novel Candidates for Early Myocardial Injury, Molecular & Cellular Proteomics, 14 at 2375-93 (2015)). In an additional embodiment, the blood plasma fraction may be one in which substantially all the clotting factors are removed in order to retain the efficacy of the fraction with reduced risk of thromboses. For example, the plasma fraction may be a plasma fraction as described in U.S. Patent No. 62/376,529 filed on Aug. 18, 2016; the disclosure of which is incorporated by reference in its entirety herein.

D. Albumin Products

To those having ordinary skill in the art, there are two general categories of Albumin Plasma Products ("APP"): plasma protein fraction ("PPF") and human albumin solution ("HAS"). PPF is derived from a process with a higher yield than HAS but has a lower minimum albumin purity than HAS (>83% for PPF and >95% for HAS). (Production of human albumin solution: a continually developing colloid, P. Matejtschuk et al., *British J. of Anaesthesia* 85(6): 887-95, at 888 (2000)). In some instances, PPF has albumin purity of between 83% and 95% or alternatively 83% and 96%. The albumin purity can be determined by electrophoresis or other quantifying assays such as, for example, by mass spectrometry. Additionally, some have noted that PPF has a disadvantage because of the presence of protein "contaminants" such as PKA. Id. As a consequence, PPF preparations have lost popularity as Albumin Plasma Products, and have even been delisted from certain countries' Pharmacopoeias. Id. Contrary to these concerns, the invention makes beneficial use of these "contaminants." Besides α, β, and γ globulins, as well as the aforementioned PKA, the methods of the invention utilize additional proteins or other factors within the "contaminants" that promote processes such as neurogenesis, neuronal cell survival, improved cognition or motor function and decreased neuroinflammation.

Those of skill in the art will recognize that there are, or have been, several commercial sources of PPF (the "Commercial PPF Preparations.") These include Plasma-Plex™ PPF (Armour Pharmaceutical Co., Tarrytown, N.Y.), Plasmanate™ PPF (Grifols, Clayton, N.C.), Plasmatein™ (Alpha Therapeutics, Los Angeles, Calif.), and Protenate™ PPF (Baxter Labs, Inc. Deerfield, Ill.).

Those of skill in the art will also recognize that there are, or have been, several commercial sources of HAS (the "Commercial HAS Preparations.") These include Albuminar™ (CSL Behring), AlbuRx™ (CSL Behring), Albutein™ (Grifols, Clayton, N.C.), Buminate™ (Baxatla, Inc., Bannockburn, Ill.), Flexbumin™ (Baxatla, Inc., Bannockburn, Ill.), and Plasbumin™ (Grifols, Clayton, N.C.).

1. Plasma Protein Fraction (Human) (PPF)

According to the United States Food and Drug Administration ("FDA"), "Plasma Protein Fraction (Human)," or PPF, is the proper name of the product defined as "a sterile solution of protein composed of albumin and globulin, derived from human plasma." (Code of Federal Regulations "CFR" 21 CFR 640.90 which is herein incorporated by reference). PPF's source material is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein).

PPF is tested to determine it meets the following standards as per 21 CFR 640.92 (incorporated by reference herein):

(a) The final product shall be a 5.0+/−0.30 percent solution of protein; and (b) The total protein in the final product shall consist of at least 83 percent albumin, and no more than 17 percent globulins. No more than 1 percent of the total protein shall be gamma globulin. The protein composition is determined by a method that has been approved for each manufacturer by the Director, Center for Biologics Evaluation and Research, Food and Drug Administration.

As used herein, "Plasma Protein Fraction" or "PPF" refers to a sterile solution of protein composed of albumin and globulin, derived from human plasma, with an albumin content of at least 83% with no more than 17% globulins (including α1, α2, β, and γ globulins) and other plasma proteins, and no more than 1% gamma globulin as determined by electrophoresis. (Hink, J. H., Jr., et al., Preparation and Properties of a Heat-Treated Human Plasma Protein Fraction, VOX SANGUINIS 2(174) (1957)). PPF can also refer to a solid form, which when suspended in solvent, has similar composition. The total globulin fraction can be determined through subtracting the albumin from the total protein. (Busher, J., Serum Albumin and Globulin, CLINICAL METHODS: THE HISTORY, PHYSICAL, AND LABORATORY EXAMINATIONS, Chapter 10, Walker H K, Hall W D, Hurst J D, eds. (1990)).

2. Albumin (Human) (HAS)

According to the FDA, "Albumin (Human)" (also referred to herein as "HAS") is the proper name of the product defined as "sterile solution of the albumin derived from human plasma." (Code of Federal Regulations "CFR" 21 CFR 640.80 which is herein incorporated by reference.) The source material for Albumin (Human) is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein). Other requirements for Albumin (Human) are listed in 21 CFR 640.80-640.84 (incorporated by reference herein).

Albumin (Human) is tested to determine if it meets the following standards as per 21 CFR 640.82:

(a) Protein concentration. Final product shall conform to one of the following concentrations: 4.0+/−0.25 percent; 5.0+/−0.30 percent; 20.0+/−1.2 percent; and 25.0+/−1.5 percent solution of protein.

(b) Protein composition. At least 96 percent of the total protein in the final product shall be albumin, as determined by a method that has been approved for each manufacturer by the Director, Center for Biologics Evaluation and Research, Food and Drug Administration.

As used herein, "Albumin (Human)" or "HAS" refers to a to a sterile solution of protein composed of albumin and globulin, derived from human plasma, with an albumin content of at least 95%, with no more than 5% globulins (including α1, α2, β, and γ globulins) and other plasma proteins. HAS can also refer to a solid form, which when suspended in solvent, has similar composition. The total globulin fraction can be determined through subtracting the albumin from the total protein.

As can be recognized by one having ordinary skill in the art, PPF and HAS fractions can also be freeze-dried or in other solid form. Such preparations, with appropriate additives, can be used to make tablets, powders, granules, or capsules, for example. The solid form can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

E. Clotting Factor-Reduced Fractions

Another embodiment of the invention uses a blood plasma fraction from which substantially all of the clotting factors are removed in order to retain the efficacy of the fraction with reduced risk of thromboses. Conveniently, the blood product can be derived from a young donor or pool of young donors and can be rendered devoid of IgM in order to provide a young blood product that is ABO compatible. Currently, plasma that is transfused is matched for ABO blood type, as the presence of naturally occurring antibodies to the A and B antigens can result in transfusion reactions. IgM appears to be responsible for transfusion reactions when patients are given plasma that is not ABO matched. Removal of IgM from blood products or fractions helps eliminate transfusion reactions in subjects who are administered the blood products and blood plasma fractions of the invention.

Accordingly, in one embodiment, the invention is directed to a method of treating a subject suffering from an unwanted condition/indication associated with any of the following: a muscle injury, muscle disease, muscle disorder, or muscle condition that could benefit from improved muscle generation, regeneration, healing, function, or restoration. The method comprises: administering to the subject a blood product or blood fraction derived from whole-blood from an individual or pool of individuals, wherein the blood product or blood fraction is substantially devoid of (a) at least one clotting factor and/or (b) IgM. In some embodiments, the individual(s) from whom the blood product or blood fraction is derived are young individuals. In some embodiments, the blood product is substantially devoid of at least one clotting factor and IgM. In certain embodiments, the blood product is substantially devoid of fibrinogen (Factor I). In additional embodiments, the blood product substantially lacks erythrocytes and/or leukocytes. In further embodiments, the blood product is substantially acellular. In other embodiments, the blood product is derived from plasma. Such embodiments of the invention are further supported by U.S. Patent Application No. 62/376,529 filed on Aug. 18, 2016, which is incorporated by reference in its entirety herein.

F. Protein-Enriched Plasma Protein Products Treatment

Additional embodiments of the invention use plasma fractions with reduced albumin concentration compared to PPF, but with increased amounts of globulins and other plasma proteins (what have been referred to by some as "contaminants"). The embodiments, as with PPF, HAS, Effluent I, and Effluent II/III, Effluent IV-1, Effluent IV-4, and Effluent V are all effectively devoid of clotting factors. Such plasma fractions are hereinafter referred to as "protein-enriched plasma protein products." For example, an embodiment of the invention may use a protein-enriched plasma protein product comprised of 82% albumin and 18% α, β, and γ globulins and other plasma proteins. Another embodiment of the invention may use a protein-enriched plasma protein product comprised of 81% albumin and 19% of α, β, and γ globulins and/or other plasma proteins. Another embodiment of the invention may use a protein-enriched plasma protein product comprised of 80% albumin and 20% of α, β, and γ globulins and/or other plasma proteins. Additional embodiments of the invention may use protein-enriched plasma protein products comprised of 70-79% albumin and a corresponding 21-30% of α, β, and γ globulins and other plasma proteins. Additional embodiments of the invention may use protein-enriched plasma protein products comprised of 60-69% albumin and a corresponding 31-40% of α, β, and γ globulins and other plasma proteins. Additional embodiments of the invention may use protein-enriched plasma protein products comprised of 50-59% albumin and a corresponding 41-50% of α, β, and γ globulins and other plasma proteins. Additional embodiments of the invention may use protein-enriched plasma protein products comprised of 40-49% albumin and a corresponding 51-60% of α, β, and γ globulins and other plasma proteins. Additional embodiments of the invention may use protein-enriched plasma protein products comprised of 30-39% albumin and a corresponding 61-70% of α, β, and γ globulins and other plasma proteins. Additional embodiments of the invention may use protein-enriched plasma protein products comprised of 20-29% albumin and a corresponding 71-80% of α, β, and γ globulins and other plasma proteins. Additional embodiments of the invention may use protein-enriched plasma protein products comprised of 10-19% albumin and a corresponding 81-90% of α, β, and γ globulins and other plasma proteins. Additional embodiments of the invention may use protein-enriched plasma protein products comprised of 1-9% albumin and a corresponding 91-99% of α, β, and γ globulins and other plasma proteins. A further embodiment of the invention may use protein-enriched plasma protein products comprised of 0% albumin and 100% of α, β, and γ globulins and other plasma proteins Embodiments of the invention described above may also have total gamma globulin concentrations of 1-5%.

The specific concentrations of proteins in a plasma fraction may be determined using techniques well-known to a person having ordinary skill in the relevant art. By way of example, and not limitation, such techniques include electrophoresis, mass spectrometry, ELISA analysis, and Western blot analysis.

G. Preparation of Plasma Fractions

Methods of preparing PPF and other plasma fractions are well-known to those having ordinary skill in the art. An embodiment of the invention allows for blood used in the preparation of human plasma protein fraction to be collected in flasks with citrate or anticoagulant citrate dextrose solution (or other anticoagulant) for inhibition of coagulation, with further separation of Fractions I, II+III, IV, and PPF as per the method disclosed in Hink et al. (See Hink, J. H., Jr., et al., Preparation and Properties of a Heat-Treated Human Plasma Protein Fraction, VOX SANGUINIS 2(174) (1957), herein incorporated by reference.) According to this method, the mixture can be collected to 2-8° C. The plasma can then subsequently be separated by centrifugation at 7° C., removed, and stored at −20° C. The plasma can then be thawed at 37° C. and fractionated, preferably within eight hours after removal from −20° C. storage.

Plasma can be separated from Fraction I using 8% ethanol at pH 7.2 and a temperature at −2 to −2.5° C. with protein concentration of 5.1 to 5.6 percent. Cold 53.3 percent ethanol (176 mL/L of plasma) with acetate buffer (200 mL 4M sodium acetate, 230 mL glacial acetic acid quantum satis to 1 L with $H_2O$) can be added using jets at a rate, for example, of 450 mL/minute during the lowering the plasma temperature to −2° C. Fraction I can be separated and removed from the effluent (Effluent I) through ultracentrifugation. Fibrinogen can be obtained from Fraction I as per methods well-known to those having ordinary skill in the art.

Fraction II+III can be separated from Effluent I through adjustment of the effluent to 21 percent ethanol at pH 6.8, temperature at −6° C., with protein concentration of 4.3 percent. Cold 95 percent ethanol (176 mL/L of Effluent I) with 10 M acetic acid used for pH adjustment can be added using jets at a rate, for example, of 500 mL/minute during the lowering of the temperature of Effluent I to −6° C. The resulting precipitate (Fraction II+III) can be removed by centrifugation at −6° C. Gamma globulin can be obtained from Fraction II+III using methods well-known to those having ordinary skill in the art.

Fraction IV-1 can be separated from Effluent II+III ("Effluent II/III") through adjustment of the effluent to 19 percent ethanol at pH 5.2, temperature at −6° C., and protein concentration of 3 percent. $H_2O$ and 10 M acetic acid used for pH adjustment can be added using jets while maintaining Effluent II/III at −6° C. for 6 hours. Precipitated Fraction IV-1 can be settled at −6° C. for 6 hours and subsequently separated from the effluent by centrifugation at the same temperature. Stable plasma protein fraction can be recovered from Effluent IV-1 through adjustment of the ethanol concentration to 30 percent at pH 4.65, temperature −7° C. and protein concentration of 2.5 percent. This can be accomplished by adjusting the pH of Effluent IV-1 with cold acid-alcohol (two parts 2 M acetic acid and one-part 95 percent ethanol). While maintaining a temperature of −7° C., to every liter of adjusted Effluent IV-1 170 mL cold ethanol (95%) is added. Proteins that precipitate can be allowed to settle for 36 hours and subsequently removed by centrifugation at −7° C. Fraction IV-4 paste/precipitate can also be attained using the Cohn fractionation process and can be resuspended. Indeed, Fraction IV-4 and its manufacturing process has been described previously (Schopfer L M, et al., *PLoS ONE*, 14(1):e0209795 (2018) and herein incorporated by reference in its entirety) (Schopfer L M, et al., *PLoS ONE*, 14(1):e0209795 (2018), and Bertolini J, Goss N, Curlin J eds., PRODUCTION OF PLASMA PROTEINS FOR THERAPEUTIC USE, 16.4: 231:232 (2013) herein incorporated by reference in their entirety).

The recovered proteins (stable plasma protein fraction) can be dried (e.g. by freeze drying) to remove alcohol and $H_2O$. The resulting dried powder can be dissolved in sterile distilled water, for example using 15 liters of water/kg of powder, with the solution adjusted to pH 7.0 with 1 M NaOH. A final concentration of 5 percent protein can be achieved by adding sterile distilled water containing sodium acetyl tryptophanate, sodium caprylate, and NaCl, adjusting to final concentrations of 0.004 M acetyl tryptophanate, 0.004 M caprylate, and 0.112 M sodium. Finally, the solution can be filtered at 10° C. to obtain a clear solution and subsequently heat-treated for inactivation of pathogens at 60° C. for at least 10 hours.

One having ordinary skill in the art would recognize that each of the different fractions and effluents described above could be used with the methods of the invention to treat conditions such as a muscle injury, muscle disease, muscle disorder, or muscle condition that could benefit from improved muscle generation, regeneration, healing, function, or restoration. For example, and not by way of limitation, Effluents I or Effluent II/III may be utilized to treat conditions such as a muscle injury, muscle disease, muscle disorder, or muscle condition that could benefit from improved muscle generation, regeneration, healing, function, or restoration and are embodiments of the invention.

The preceding methods of preparing plasma fractions and plasma protein fraction (PPF) are only exemplary and involve merely embodiments of the invention. One having ordinary skill in the art would recognize that these methods can vary. For example, pH, temperature, and ethanol concentration, among other things can be adjusted to produce different variations of plasma fractions and plasma protein fraction in the different embodiments and methods of the invention. In another example, additional embodiments of the invention contemplate the use of nanofiltration for the removal/inactivation of pathogens from plasma fractions and plasma protein fraction.

An additional embodiment of the invention contemplates methods and composition using and/or comprising additional plasma fractions. For example, the invention, among other things, contemplates that specific concentrations of albumin are not critical for treating conditions associated with a muscle injury, muscle disease, muscle disorder, or muscle condition that could benefit from improved muscle generation, regeneration, healing, function, or restoration. Hence, fractions with reduced albumin concentration, such as those fractions having below 83% albumin, are contemplated by the invention.

H. Treatment

Aspects of the methods of the inventions described herein include treatment of a subject with a plasma comprising blood product, such as a blood plasma fraction, e.g., as described above. An embodiment includes treatment of a human subject with a plasma comprising blood product. One of skill in the art would recognize that methods of treatment of subjects with plasma comprising blood products are recognized in the art. By way of example, and not limitation, one embodiment of the methods of the inventions described herein is comprised of administering fresh frozen plasma to a subject for treatment of conditions such as muscle injury, muscle disease, muscle disorder, or muscle condition that could benefit from improved muscle generation, regeneration, healing, function, or restoration. In one embodiment, the plasma comprising blood product is administered immediately, e.g., within about 12-48 hours of collection from a donor, to the individual suffering from a muscle injury, muscle disease, muscle disorder, or muscle condition that could benefit from improved muscle generation, regeneration, healing, function, or restoration. In such instances, the product may be stored under refrigeration, e.g., 0-10° C. In another embodiment, fresh frozen plasma is one that has been stored frozen (cryopreserved) at −18° C. or colder. Prior to administration, the fresh frozen plasma is thawed and once thawed, administered to a subject 60-75 minutes after the thawing process has begun. Each subject preferably receives a single unit of fresh frozen plasma (200-250 mL), the fresh frozen plasma preferably derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old.

In an embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In yet another embodiment of the invention, the subject is treated with a Plasma Fraction. In an embodiment of the invention, the plasma fraction is a PPF, HAS, Fraction IV-4 or Fraction IV-4 paste suspension. In a further embodiment of the invention, the plasma fraction is one of the Commercial PPF Preparations of the Commercial HAS Preparations. In another embodiment of the invention the plasma fraction is a PPF, HAS, Fraction IV-4 or Fraction IV-4 paste suspension derived from a pool of individuals of a specific age range, such as young individuals, or is a modified PPF, HAS, Fraction IV-4 or Fraction IV-4 paste suspension fraction which has been subjected to additional fractionation or processing (e.g. PPF, HAS, Fraction IV-4 or Fraction IV-4 paste suspension with one or more specific proteins partially or substantially removed). In another embodiment of the invention, the plasma fraction is an IGIV plasma fraction which has been substantially depleted of immune globulin (IgG). A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

I. Administration

Aspects of the methods of the inventions described herein include treatment of a subject with a plasma comprising blood product, such as a blood plasma or Plasma Fraction, e.g., as described above. An embodiment includes treatment of a human subject with a plasma comprising blood product. One of skill in the art would recognize that methods of treatment of subjects with plasma comprising blood products are recognized in the art. By way of example, and not limitation, one embodiment of the methods of the inventions described herein is comprised of administering fresh frozen plasma to a subject for treatment of a muscle injury, muscle disease, muscle disorder, or muscle condition that could benefit from improved muscle generation, regeneration, healing, function, or restoration. In one embodiment, the plasma comprising blood product is administered immediately, e.g., within about 12-48 hours of collection from a donor, to the individual suffering from an unwanted condition such as a muscle injury, muscle disease, muscle disorder, or muscle condition that could benefit from improved muscle generation, regeneration, healing, function, or restoration. In such instances, the product may be stored under refrigeration, e.g., 0-10° C. In another embodiment, fresh frozen plasma is one that has been stored frozen (cryopreserved) at −18° C. or colder. Prior to administration, the fresh frozen plasma is thawed and once thawed, administered to a subject 60-75 minutes after the thawing process has begun. Each subject preferably receives a single unit of fresh frozen plasma (200-250 mL), the fresh frozen plasma preferably derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old.

In an embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In yet another embodiment of the invention, the subject is treated with a Plasma Fraction. In an embodiment of the invention, the plasma fraction is PPF or HAS. In a further embodiment of the invention, the plasma fraction is one of the Commercial PPF Preparations or the Commercial HAS Preparations. In another embodiment of the invention the plasma fraction is a PPF or HAS derived from a pool of individuals of a specific age range, such as young individuals, or is a modified PPF or HAS fraction which has been subjected to additional fractionation or processing (e.g. PPF or HAS with one or more specific proteins partially or substantially removed). In another embodiment of the invention, the plasma fraction is an IGIV plasma fraction which has been substantially depleted of immune globulin (IgG). A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

An embodiment of the invention includes treating a subject suffering from muscle injury, muscle disease, muscle disorder, or muscle condition that could benefit from improved muscle generation, regeneration, healing, function, or restoration by administering to the subject an effective amount of blood plasma or Plasma Fraction. Another embodiment of the invention includes administering the effective amount of blood plasma or Plasma Fraction and subsequently monitoring the subject for improved function, wound healing, the presence of markers, decreased pain, or decreased inflammation. Another embodiment of the invention includes treating a subject suffering from a condition as muscle injury, muscle disease, muscle disorder, or muscle condition that could benefit from improved muscle generation, regeneration, healing, function, or restoration by administering to the subject an effective amount of blood plasma or Plasma Fraction wherein the blood plasma or Plasma Fraction is administered in a manner resulting in improved function wound healing, the presence of markers, decreased pain, or decreased inflammation after the mean or median half-life of the blood plasma proteins or Plasma Fraction proteins been reached, relative to the most recent administered dose (referred to as "Pulsed Dosing" or "Pulse Dosed" herein) (See U.S. patent application Ser. No. 15/499, 697 and Ser. No. 62/701,411, which are herein incorporated by reference in their entirety). Another embodiment of the invention includes administering the blood plasma or Plasma Fraction via a dosing regimen of at least two consecutive days and monitoring the subject for improved function or HSC marker levels at least 3 days after the date of last administration. A further embodiment of the invention includes administering the blood plasma or Plasma Fraction via a dosing regimen of at least 3, 4, 5, 6, 7, 8, 9, 10, 11, 12, 13, or 14 consecutive days and monitoring the subject for improved function, wound healing, the presence of markers, decreased pain, or decreased inflammation at least 3 days after the date of last administration. Yet another embodiment of the invention includes administering the blood plasma or Plasma Fraction via a dosing regimen of at least 2 consecutive days and after the date of last administration, monitoring for functional improvement, wound healing, the presence of markers, decreased pain, or decreased inflammation beyond when the average half-life of the proteins in the blood plasma or Plasma Fraction has been reached. Another embodiment of the invention includes administering the blood plasma or Plasma Fraction via a dosing regimen of 2 to 14 non-consecutive days wherein each gap between doses may be between 0-3 days each.

In some instances, Pulsed Dosing in accordance with the invention includes administration of a first set of doses, e.g., as described above, followed by a period of no dosing, e.g., a "dosing-free period," which in turn is followed by administration of another dose or set of doses. The duration of this "dosing-free" period, may vary, but in some embodiments, is 7 days or longer, such as 10 days or longer, including 14 days or longer, wherein some instances the dosing-free period ranges from 15 to 365 days, such as 30 to 90 days and including 30 to 60 days. As such, embodiments of the methods include non-chronic (i.e., non-continuous) dosing, e.g., non-chronic administration of a blood plasma product. In some embodiments, the pattern of Pulsed Dosing followed by a dosing-free period is repeated for a number of times, as desired, where in some instances this pattern is continued for 1 year or longer, such as 2 years or longer, up to and including the life of the subject. Another embodiment of the invention includes administering the blood plasma or Plasma Fraction via a dosing regimen of 5 consecutive days, with a dosing-free period of 2-3 days, followed by administration for 2-14 consecutive days.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances, reverse unwanted conditions such as such as a muscle injury, muscle disease, muscle disorder, or muscle condition that could benefit from improved muscle generation, regeneration, healing, function, or restoration.

J. Plasma Protein Fraction

In practicing methods of the invention, a plasma fraction is administered to the subject. In an embodiment, the plasma fraction is plasma protein fraction (PPF). In additional embodiments, the PPF is selected from the Commercial PPF Preparations.

In another embodiment, the PPF is comprised of 88% normal human albumin, 12% alpha and beta globulins and not more than 1% gamma globulin as determined by electrophoresis. Further embodiments of this embodiment used in practicing methods of the invention include, for example, the embodiment as a 5% solution of PPF buffered with sodium carbonate and stabilized with 0.004 M sodium caprylate and 0.004 M acetyltryptophan. Additional formulations, including those modifying the percentage of PPF (e.g. about 1% to about 10%, about 10% to about 20%, about 20% to 25%, about 25% to 30%) in solution as well as the concentrations of solvent and stabilizers may be utilized in practicing methods of the invention.

K. Plasma Fractions of Specific Donor Age

Additional embodiments of the invention include administering a plasma protein fraction derived from the plasma of individuals of certain age ranges. An embodiment includes administering PPF or HAS which have been derived from the plasma of young individuals. In another embodiment of the invention the young individuals are of a single specific age or a specific age range. In yet another embodiment, the average age of the donors is less than that of the subject or less than the average age of the subjects being treated.

Certain embodiments of the invention include pooling blood or blood plasma from individuals of specific age ranges and fractionating the blood plasma as described above to attain a plasma protein fraction product such as PPF or HAS. In an alternate embodiment of the invention, the plasma protein fraction or specific plasma protein fraction is attained from specific individuals fitting a specified age range.

L. Indications

An embodiment of the invention is using plasma fractions and products of blood plasma fractionation to administer to a subject diagnosed with a disease, condition, or disorder that could benefit from improved muscle generation, regeneration, healing, function, or restoration. A further embodiment of the invention includes treating a disease, condition, or disorder when said disease or disorder is: muscle atrophy or weakness (by way of example and not limitation—from exacerbation by exercise or immobilization); sarcopenia; cachexia; McArdle disease; weakness associated with stroke; degeneration associated with amyotrophic lateral sclerosis; neuromuscular junction disorders; myasthenia gravis; toxic myopathies; inflammatory myopathies; lipid storage myopathies; acute physical or chemical injury; ischemia/reperfusion (e.g. organ-transplantation surgery, stroke, hypovolemic shock); contraction-induced damages; genetic-related degenerative disease; Duchenne and Becker muscular dystrophies; myotonic dystrophy; limb girdle muscular dystrophy; Emery-Dreifuss muscular dystrophy; congenital muscular dystrophy; and facioscapulohumeral muscular dystrophy.

Further embodiments of the invention include treating the disease or disorder when said disease, disorder, or condition is: acute muscle injury from a single traumatic event such as sports, contact sports, or traumatic accident such as from a collision (see Bahr, R., Mccrory, P., LaPrade, R. F., Meeuwisse, W. H., & Engebretsen, L. (2012). *The IOC manual of sports injyuries: an illustrated guide to the management of injuries in physical activity*. Wiley and Sons. 2012, hereby incorporated by reference in its entirety); overuse injuries such as from chronic use or exercise-induced use where repetitive microtrauma occurs to the muscle; muscle strain or sprain including Grade I (Mild—with a small number of muscle fibers involved), Grade II (Moderate—involving a significant number of muscle fibers torn with pain reproduced on muscle contraction and limited movement due to pain), and Grade III (Severe—a complete tear or rupture where either the tendon is separated from the muscle belly or the muscle belly is torn in 2 or more parts); muscle contusion or bruise; muscle cramps or spasms (sudden involuntary muscle contractions or over-shortening); and muscle soreness including delayed onset muscle soreness (DOMS).

Further embodiments of the invention include treatment of a muscle disease, disorder, or condition with administration of plasma fractions and products of blood plasma fractionation in combination with traditional treatments. Embodiments of the invention may include said combination treatment using the RICE (Rest, Ice, Compression, Elevation) or POLICE (Protection, Rest, Ice, Compress, Elevate) principles. Further embodiments may include treatment with plasma fractions/products of blood plasma fractionation in combination with surgical intervention or physical therapy. The combination of treatment with plasma fractions/products of blood plasma fractionation with more traditional treatments may occur concurrently or with the traditional treatment(s) occurring before and/or after administration of the plasma fractions/products of blood plasma fractionation.

Another embodiment of the invention includes diseases, conditions, or disorders of the cardiac muscle including by way of example and not limitation the reduction of cardiac hypertrophy. Further examples of cardiac-related diseases, conditions, or disorders include cardiomyopathy (enlarged heart), dilated cardiomyopathy, hypertrophic cardiomyopathy, restrictive cardiomyopathy, congenital heart disease, heart attack, and hypertension.

M. Reagents, Devices, and Kits

Also provided are reagents, devices, and kits thereof for practicing one or more of the above-described methods. The subject reagents, devices, and kits thereof may vary greatly.

Reagents and devices of interest include those mentioned above with respect to the methods of preparing plasma-comprising blood product for transfusion into a subject in need hereof, for example, anti-coagulants, cryopreservatives, buffers, isotonic solutions, etc.

Kits may also comprise blood collection bags, tubing, needles, centrifugation tubes, and the like. In yet other embodiments, kits as described herein include two or more containers of blood plasma product such as plasma protein fraction, such as three or more, four or more, five or more, including six or more containers of blood plasma product. In some instances, the number of distinct containers of blood plasma product in the kit may be 9 or more, 12 or more, 15 or more, 18 or more, 21 or more, 24 or more 30 or more, including 36 or more, e.g., 48 or more. Each container may have associated therewith identifying information which includes various data about the blood plasma product contained therein, which identifying information may include one or more of the age of the donor of the blood plasma product, processing details regarding the blood plasma product, e.g., whether the plasma product was processed to remove proteins above an average molecule weight (such as described above), blood type details, etc. In some instances, each container in the kit includes identifying information about the blood plasma contained therein, and the identifying information includes information about the donor age of the blood plasma product, e.g., the identifying information provides confirming age-related data of the blood plasma product donor (where such identifying information may be the age of the donor at the time of harvest). In some instances, each container of the kit contains a blood plasma product from a donor of substantially the same age, i.e., all of the containers include product from donors that are substantially the same, if not the same, age. By substantially the same age is meant that the various donors from which the blood plasma products of the kits are obtained differ in each, in some instances, by 5 years or less, such as 4 years or less, e.g., 3 years or less, including 2 years or less, such as 1 year or less, e.g., 9 months or less, 6 months or less, 3 months or less, including 1 month or less. The identifying information can be present on any convenient component of the container, such as a label, an RFID chip, etc. The identifying information may be human readable, computer readable, etc., as desired. The containers may have any convenient configuration. While the volume of the containers may vary, in some instances the volumes range from 10 ml to 5000 mL, such as 25 mL to 2500 mL, e.g., 50 ml to 1000 mL, including 100 mL to 500 mL. The containers may be rigid or flexible, and may be fabricated from any convenient material, e.g., polymeric materials, including medical grade plastic materials. In some instances, the containers have a bag or pouch configuration. In addition to the containers, such kits may further include administration devices, e.g., as described above. The components of such kits may be provided in any suitable packaging, e.g., a box or analogous structure, configured to hold the containers and other kit components.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

N. EXPERIMENTAL EXAMPLES

1. Example 1 a) Short Term Treatment

C2C12 myoblast cells (Sigma Aldrich 91031101-1VI) were plated on day minus two (d-2) at 8,000 cells per well on a 96-well plate in C2C12 media (DMEM+GlutaMAX (ThermoFisher Scientific)+4.5 g/L glucose, 10% fetal bovine serum (FBS), 1% penicillin-streptomycin (P/S)). After two days a complete media change was made using C2C12 differentiation media (DMEM+GlutaMAX+1 g/L glucose, 2% horse serum (Gibco), 1% P/S). The addition of differentiation media results in C2C12 myoblast fusion and differentiation into myotubes. This was designated as day zero (d0) (See FIG. 2). At day 5 (d5) the treatment assay was started by removing media completely from each well and by adding 150 µL of the different media plus treatments: (1) untreated; (2) 1 mM Metformin (positive control—MedChem Express HY-17471A/C8-1851); (3) 0.5 mM Metformin; (4); 0.25 mM Metformin; (5) vehicle (10% in media); (6) PPF1 (5 mg/mL in media); (7) HAS1 (5 mg/mL in media); and (8) recombinant human Albumin (rhAlbumin 5 mg/mL in media).

PPF1 is a PPF with approximately 88% normal human albumin (in relation to total protein), 12% alpha and beta globulins, and no more than 1% gamma globulin as determined by electrophoresis. Except where noted, PPF1 is administered in the examples herein using a 5% solution (w/v, 50 g/L). HAS1 is a commercially available HAS such as those Commercial HAS Preparations described above in 5% solution and were stored at 4° C.

Twenty-four hours later, a glucose utilization assay was performed using a glucose assay kit (Abcam—ab65333). First, a pre-test of glucose utilization was performed to specify the appropriate dilution of the media. Therefore, 100 µL of media from untreated cells was removed and the supernatant was diluted in an assay buffer (1:1/1:2/1:5/1:10 with a final volume of 50 µL/well). The reaction agent was subsequently added (46 µL) plus 2 µL substrate and 2 µL enzyme per well. After the correct dilution was determined, media from all treatment groups and another untreated control was diluted accordingly with final volume being 50 µL/well.

A glucose standard curve from the Abcam kit was pipetted into wells and reaction mix was added to the standard and treatment samples (46 µL assay buffer+2 µL substrate+2 µL enzyme per well). The reaction was incubated for 30 minutes at 37° and absorbance subsequently measured at 570 nm. The concentration of glucose was calculated based on the standard.

Figure 3A:
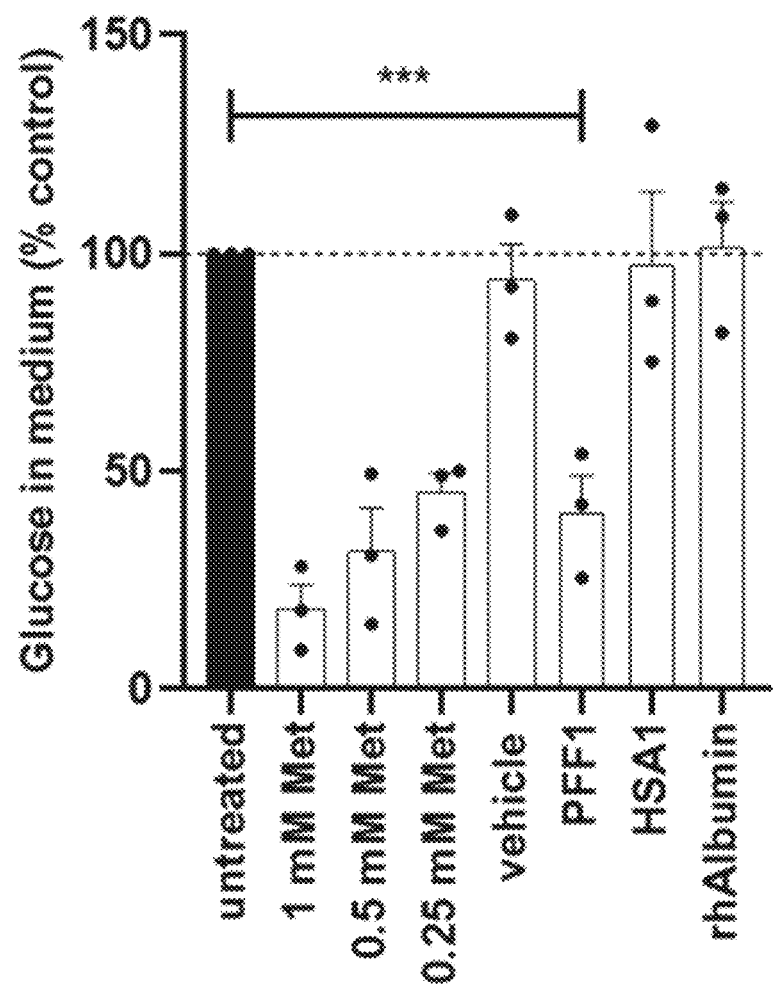
FIG. 3B is a still photo capture of video of myotubes treated with PPF1 as described in FIGS. 2 and 3A.

FIG. 3A shows the glucose utilization by concentration (% OD) remaining in the medium. PPF1-treated cells showed a distinct increase in glucose utilization compared to vehicle and other plasma fractions (e.g. HAS1). It was also observed that PPF1 trended towards enhancing contraction of myotubes to a greater degree than HAS1 or rhAlbumin. Thus, PPF1 enhances cellular metabolism distinct from HAS1 and rhAlbumin. Data were n=3 wells from three independent experiments ±SEM.

Figure 1:
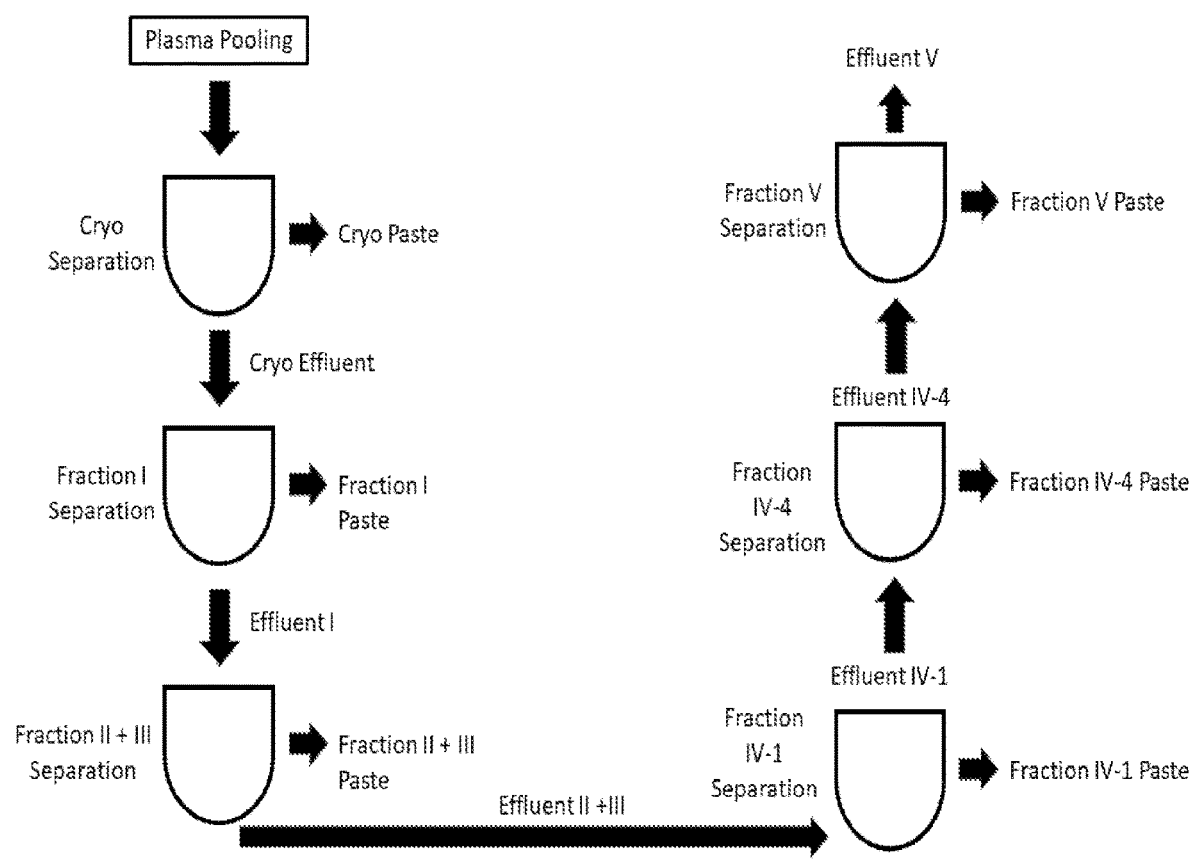
Figure 2:
Figure 3B:
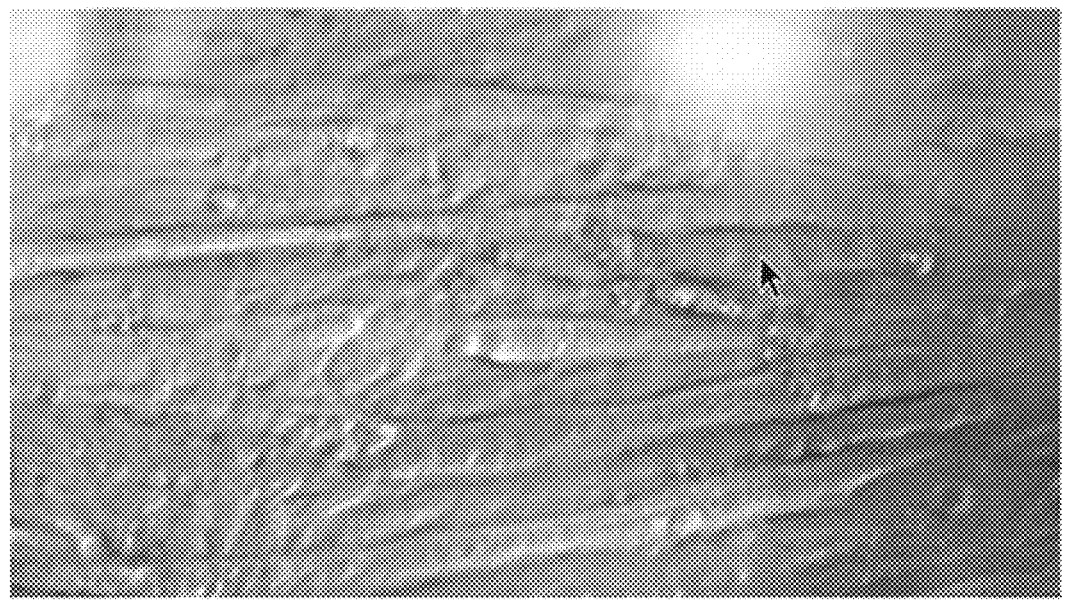

FIG. 3B is a still photo capture of video of myotubes treated with PPF1 as described in FIGS. 2 and 3A. Markedly increased contraction over untreated and vehicle controls was observed. This correlates with skeletal muscle recovery from conditions/indications such as aging muscle, frailty, and muscle recovery during and after surgery.

2. Example 2 a) Long Term Treatment with Different Horse Serum Concentrations

Figure 4:
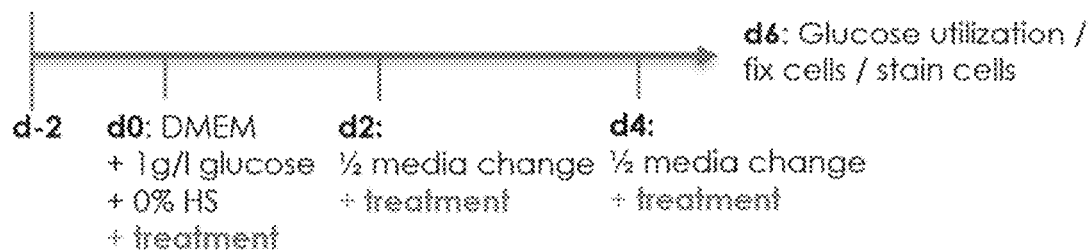
FIG. 4 depicts the design of a long-term media treatment using either 0% or 2% horse serum, with a glucose utilization assay commencing six days after the start of treatment and 48 hours after the last administration of treatment.

FIG. 4 shows a representation of an experiment testing the effect of different horse serum concentrations on C2C12 cells in culture. It was hypothesized that the effect of PPF1 may be resolve to a higher degree if the level of horse serum were decreased. On Day −2, C2C12 myoblast cells (Sigma Aldrich 91031101-1VI) were plated on day minus two (d-2) at 8,000 cells per well on a 96-well plate in C2C12 media (DMEM+GlutaMAX (ThermoFisher Scientific)+4.5 g/L glucose, 10% fetal bovine serum (FBS), 1% penicillin-streptomycin (P/S)). After two days a complete media change was made using C2C12 media with or without 2% horse serum (DMEM+GlutaMAX+1 g/L glucose, 0% or 2% horse serum (Gibco), 1% P/S) plus treatment: (1) untreated; (2) vehicle (10% in media); (3) PPF1 (5 mg/mL in media); (4) HAS1 (5 mg/mL in media); and (5) recombinant human Albumin (rhAlbumin 5 mg/mL in media). This was designated as day zero (d0). At day 2 (d2) half the media was removed and replenished along with same concentrations of treatments (5 mg/mL). On day 4 (d4) half the media was again removed and replenished along with same concentrations of treatments (5 mg/mL). On day 6 (d6) the glucose utilization assay was performed as were cell fixing and staining.

Figure 5:
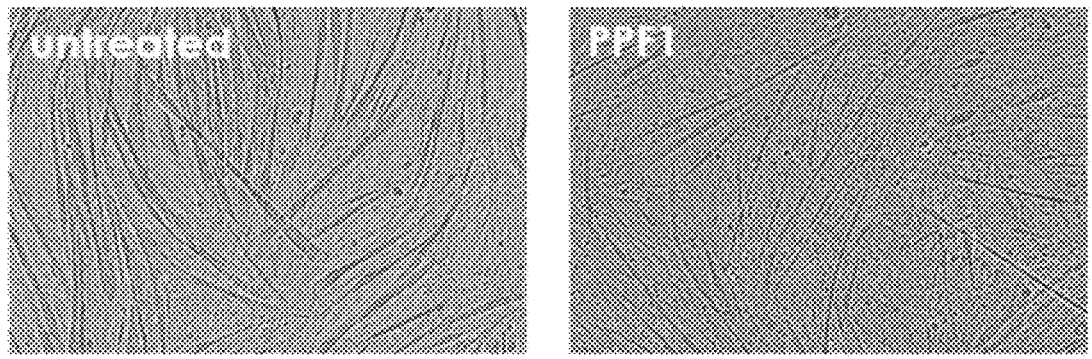
FIG. 5 shows micrographs of C2C12 cells cultured in 0% or 2% horse serum (HS) as per the experimental design depicted in FIG. 4. Treatment with PPF1 with 0% horse serum concentration resulted in a greater amount of myotube formation than untreated.
Figure 5:
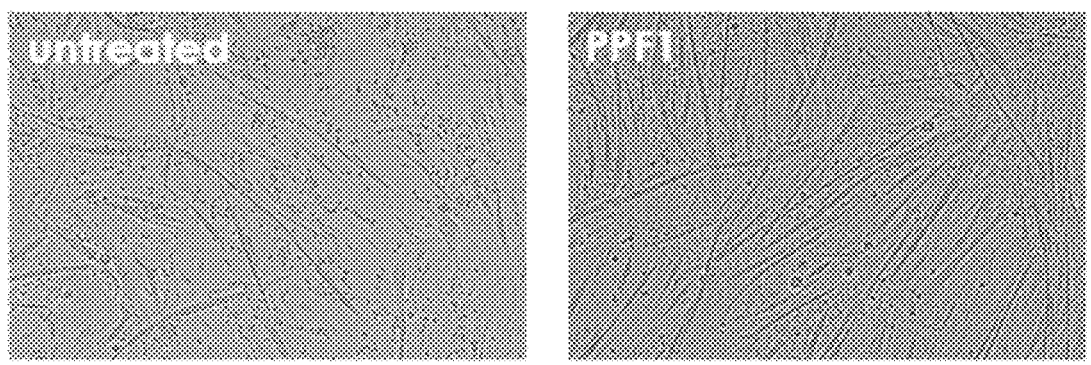

FIG. 5 shows C2C12 cells in culture in both 0% horse serum and 2% horse serum. For each horse serum concentration, untreated and PPF1-treated cells are represented.

Figure 6:
FIG. 6 shows that C2C12 cells treated with 0% horse serum and PPF1 exhibit positive staining for the myogenic differentiation marker, Myosin Heavy Chain.

Treatment with PPF1 in both serum concentrations resulted in a greater amount of myotube formation, and thus differentiation of C2C12 cells into myotubes, with 0% horse serum, untreated C2C12 cells exhibiting the least amount of myotube differentiation. FIG. 6 shows that the C2C12 cells treated with 0% horse serum and PPF1 exhibited positive staining for the myogenic differentiation marker, Myosin Heavy Chain.

FIG. 7 reports the glucose utilization by concentration (% OD) remaining in the medium of C2C12 cells treated long term in 0% horse serum. Despite the absence of horse serum, PPF1-treated cells showed a distinct increase in glucose utilization compared to vehicle and other plasma fractions (e.g. HAS1). It was also observed that PPF1 trended towards enhancing contraction of myotubes to a greater degree than HAS1 or rhAlbumin. Thus, PPF1 enhances cellular metabolism distinct from HAS1 and rhAlbumin. Data were n=4 wells from three independent experiments ±SEM.

FIG. 8 reports glucose utilization by concentration (% OD) remaining in the medium of C2C12 cells treated long term with 0% horse serum and different plasma fractions and products from plasma fractionation. The treatment regimen was performed as described in FIG. 4 above, but with treatments being: (1) untreated; (2) PPF1 (5 mg/mL in media); (3) Filtrate IV-4 (5 mg/mL in media); and (4) Fraction IV-4 paste suspension (5 mg/mL in media; concentrated dialysate of IV-1 suspension dialyzed with 0.9% NaCl/10 mM HEPES pH 7.3) corresponding to the Cohn fractionation process. The results show that two plasma fractions/fractionation products exhibited a similar effect as PPF1 in glucose utilization in C2C12 cells.

FIG. 9 shows the relative expression of glucose transporter type 4 (GLUT-4), a protein with a key role in regulating whole body glucose homeostasis in C2C12 myoblasts either untreated or treated with control vehicle, PPF1 (5 mg/mL in media), or recombinant human albumin (rhAlbumin 5 mg/mL in media) 10% solution (w/v/, 50 g/L). Data is n=2 wells from one experiment ±***p<0.001.

FIG. 10 reports a dose-response relationship between the plasma fractions/fractionation products described in FIG. 8 and glucose utilization. C2C12 myoblasts were differentiated to myotubes in 0% horse serum differentiation media for 6 days in vitro. Different treatment concentrations were added to cells (0.15, 0.3, 0.6, 1.25, 2.5, 5, and 10 mg/mL in the media). After 6 days of treatment and 48 hours with the same media, the amount of glucose left in the media was analyzed by the glucose utilization assay described previously above. All three compositions exhibited a dose-response relationship to glucose utilization, with Fraction IV-4 paste suspension exhibiting strongest median efficacy ($EC_{50}$).

3. Example 3 a) Short Term In Vivo Administration of PPF1 Increases Muscle Mass and Induces Slow Twitch Fiber-Associated Genes FIG. 11A is a summary table of several experiments performed on C57BL/6 mice of various ages as well as young rats and tested for muscle weight values of the tibialis anterior, extensor digitorum longus, gastrocnemius, and soleus muscles. Each experiment also tested the effects of muscle weight on varying lengths of time after the last dose treatment with vehicle or PPF1. The table shows that significant muscle weight increases are associated with PPF1 treatment with sustained effects even observed for long periods after the most recent dose.

FIG. 11B is a representation of an experimental protocol to investigate muscle-related metrics on 22-month-old male C57B6 mice treated with PPF1 or control. Male C57B6 mice at 26 months of age were pulse dosed with PPF1 or control vehicle for 7 consecutive days (150 µL per dose, i.v.). Ten (10) days after the last dose, the following skeletal muscle groups were harvested: tibialis anterior (TA), extensor digitorum longus (EDL), and soleus (SOL). From each muscle group, the muscle to body weight (BW) ratio was obtained. FIG. 11C shows that the tibialis anterior muscle tissue significantly gained weight with PPF1 treatment compared to control (mean±SEM, p<0.01 Welch's test). FIG. 11D shows that the extensor digitorum longus muscle tissue significantly gained weight with PPF1 treatment compared to control (mean±SEM, p<0.01 Welch's test). FIG. 11E shows that the soleus muscle tissue significantly gained weight with PPF1 treatment compared to control (mean±SEM, *p<0.05 Welch's test).

FIG. 12A shows that PPF1 can induce slow twitch fiber genes (Myl2(2a)) in tibialis anterior muscle. In contrast, fast twitch fiber genes (Myh1(2×) and Myh2(2a)) trended towards decreased expression in mice treated with PPF1 (See FIG. 12B and FIG. 12C, respectively). FIG. 12D shows that there was a slight decreased trend in the fast twitch muscle fiber-associated gene, Myh4(2b).

Increased slow-twitch fibers is a hallmark of endurance phenotypes. When mice or humans undergo exercise training, slow twitch fibers are increased, and fast twitch fibers are decreased. Slow twitch fibers are more fatigue resistant, burning more fat than fast twitch fibers. This also implicates an association for treatment with obesity-related diseases since if PPF1 promotes formation of slow twitch fibers it would function much like other known exercise-mimetics such as Metformin, AICAR, and resveratrol.

4. Example 4 a) Effects of PPF1 and Fraction IV-1 Paste Suspension Myotube Formation

FIG. 13A, FIG. 13B, FIG. 13C, and FIG. 13D all show C2C12 cells after 3 days of culture in 0% horse serum in conjunction with various treatment conditions. FIG. 13A shows the C2C12 cells in untreated conditions. FIG. 13B shows C2C12 cells treated with 0.3% PPF1 for 3 days. FIGS. 13C and 13D show C2C12 cells treated with 0.3% IV-1 paste suspension and 1.25% IV-1 paste suspension respectively for 3 days.

Comparison between 0.3% PPF1-treated and 0.3% IV-1 paste suspension-treated C2C12 cells shows that after 3 days, IV-1 paste suspension induced greater myotube formation than PPF1 at the same concentration. FIG. 13D also shows that the induction by IV-1 paste suspension was dose-dependent since a visual increase in myotube formation appeared to cause an increase in myotube formation (1.25% vs. 0.3% treatment concentration). All three treatment conditions (0.3% PPF1, 0.3% IV-1 paste suspension, and 1.25% IV-1 paste suspension) visually produced more myotube formation than vehicle alone.

FIG. 14 reports the dose-response relationship between plasma fractions/fractionation products by normalized glucose utilized (%) of C2C12 cells grown in 0% horse serum for six days. The x-axes depict increasing doses of IV-1 paste suspension, PPF1, and IV-1 effluent. $EC_{50}$ values are also reported, with IV-1 paste suspension having the most efficacy (0.1 mg/ml), IV-1 effluent having the next highest efficacy (0.4 mg/ml), and PPF1 having the lowest efficacy yet still being highly effective (1.4 mg/ml).

FIG. 15A, FIG. 16B, and FIG. 16C reports the dose-response relationship between plasma fractions/fractionation products by normalized glucose utilized (%) glucose utilization by concentration (% OD) remaining the medium of C2C12 cells grown in 2% horse serum for six days. The x-axes depict increasing doses of IV-1 paste suspension, PPF1, and IV-1 effluent (concentration tested: 5, 2.5, 1.25. 0.6, 0.3, 0.15, 0.075 mg/ml), respectively for each figure. $EC_{50}$ values are also reported, with IV-1 paste suspension having the most efficacy (0.4 mg/ml), IV-1 effluent having the next highest efficacy (1.7 mg/ml), and PPF1 having the lowest efficacy yet still being highly effective (3.8 mg/ml %).

5. Example 5 a) Effects of IGF1 on Metabolic Activity

FIG. 16A and FIG. 16B report the effects of insulin-like growth factor-1 (IGF-1) on glucose utilization in C2C12 cells treated in 2% horse serum. Cells were plated in DMEM plus 4.5 g/L of glucose and 10% fetal bovine serum (FBS) at Day −2 (d-2). At Day 0 (d0) media was refreshed with DMEM plus 1 g/L glucose and 2% horse serum. At Day 5 (d5) various treatments were added with glucose utilization determined at Day 6 (d6). FIG. 16A reports the dose-response relationship between recombinant human IGF-1 treatment (x-axis) and glucose utilization, revealing an EC50 of 17.43 ng/mL. Recombinant human IGF1 was purchased from R&D Systems (Cat. 291-G1). FIG. 16B reports the dose-response relationship between PPF1 treatment and glucose utilization, revealing an $EC_{50}$ of 2.9 mg/ml containing 0.87 ng/mL IGF1. IGF-1 is known to have an impact on metabolism of myotubes, and its presence in PPF1 has been calculated as approximately 14.88 ng/mL. However, the data presented here reveals that PPF1 has 20× more efficacy than IGF-1 alone, thus the presence of IGF-1 alone cannot explain the enhanced efficacy observed with PPF1. Thus, other factors must necessarily be involved in the effects of PPF1.

6. Example 6 a) PPF1 Improves Muscle Recovery from Injury

FIG. 17A is a representation of an experimental protocol to investigate muscle recovery from an injury using different treatments. To induce muscle injury in vivo, C57BL/6 mice were anesthetized by isoflurane inhalation. At day 2 of test article dosing, left tibialis anterior muscles were injected with 50 μL of $BaCl_2$ solution (Sigma-Aldrich B0750, 1.2% in sterile 0.9% NaCl) throughout the length of the tibia with a 30-gauge insulin syringe. Right tibialis anterior muscles were injected with 50 μL of saline as contralateral uninjured controls.

Left hindlimbs were wrapped with 2 layers of surgical tape and sports tape (Durapore 3M 1538-2 and Hampton Adams 8542028768) during the immobilization phase for 10 days and unwrapped during the recovery phase for 10 days. An aversive spray (Grannick's bitter apple, GB11A8T) was applied to the tape's outer surface to discourage mice from chewing at and removing the tape. Animals were monitored daily for toe circulation and tape integrity.

The hindlimb of each anesthetized mouse was prepare for torque measurements above the ankle as described previously (Gerlinger-Romero F, et al., *J. Vis. Exp.* 58696 (2019), doi:10.3791/58696)). Twitch force and tetanus force were recorded with the settings as described previously. (Ho A T V et al., *PNAS*, 114:6675-84 (2017)). Both the left and hind limbs were recorded prior to dosing for baseline measurements, and values at the end of the study (day 17) compared to the initial readings (day 0).

For systemic treatments, animals were pulse dosed i.v. with 150 50 μL of test treatments for 7 consecutive days. Vehicle, PPF1, HAS1, and recombinant human albumin (rhAlbumin) were administered to different cohorts.

FIG. 17B reports the results of the twitch force measurements taken a day 0 and day 17. At day 0 (prior to dosing), all four cohorts' twitch force readings produced similar maximum torque values. At day 17 however, only the PPF1-treated cohort produced significantly increased maximal torque compared to control vehicle. Both recombinant human albumin (rhAlbumin) and HAS1 failed to produce a change maximal torque that was significantly increased compared to control vehicle. Data is mean±SEM, *$p<0.05$ Welch's t-test.

7 Example 7 a) PPF1 Associated with Increased IGF-1 Serum Levels

FIG. 18A is a representation of an experimental protocol to investigate the effects of plasma fractions on serum mouse IGF1 levels. 22-month-old C57BL/6 mice treated as described in Example 9 had blood collected 10 days after the last day of a 7 consecutive day pulse dose treatment with PPF1. The blood serum was isolated, and levels of mouse IGF-1 determined. FIG. 18B reveals that PPF1 treatment, even 10 days after the last dose, is associated with significantly increased mouse IGF-1 in the serum, suggesting one of possibly several mechanisms through which plasma fractions such as PPF1 can induce skeletal muscle recovery from injury as induced in a $BaCl_2$ injury-induced model. Data is mean±SEM, *$p<0.05$ Welch's t-test.

8. Example 8 a) PPF1 Decreases Aged Heart Weight In Vivo

FIG. 19A is a representation of an experimental protocol to investigate whether plasma fractions can decrease heart weight in aged C57BL/6 mice, in a model of hypertrophic cardiac muscle observed in aged mammals. (See Kiper C et al., PLoS ONE 8(8): e70512). 26-month-old mice treated with a pulse dose of PPF1 for seven consecutive days were sacrifice at Day 17 and heart weights measured. FIG. 19B shows heart weight in milligrams for both vehicle and PPF1 treated mice. PPF treated mice exhibited significantly reduced heart weights compared to controls, indicating that age-related hypertrophy can be decreased with plasma fractions such as PPF1. FIG. 19C shows the heart weight to body weight ratios of the same mice, with the ratios significantly reduced in PPF1 treated mice compared to controls, also indicating a reduction in age-related hypertrophy.

FIG. 20A, FIG. 20B, and FIG. 20C report expression of cardio-protective marker RNA levels in the hearts described in FIGS. 19A, 19B, and 19C. FIG. 20A shows that RNA expression of sarco-endoplasmic reticulum calcium-ATPase (SERCA2a) significantly increases with PPF1 treatment compared to control. SERCA2a is a critical modulator of contractility and nodal calcium cycling protein the pathogenesis of heart failure. Its reduction is associated with heart failure with gene therapy restoration being associated with promising clinical results in subjects with the indication. (Chaanine A H et al., Stem Cell and Gene Therapy for Cardiovascular Disease—Chapter 30—SERACA2a Gene Therapy for Heart Failure, 389-400 (2016)). FIG. 20B shows that RNA expression of peroxisome proliferator activated receptor gamma coactivator 1 alpha (PGC1a) significantly increases with PPF1 treatment compared to control. PGC1a repression is associated with heart failure. (Riehle C and Abel D, Trends Cardiovasc Med, 22(4):98-105 (2012)). FIG. 20C shows that RNA expression of α-myosin heavy chain (aMHC) significantly increases with PPF1 treatment compared to control. Decline of aMHC is associated with cardiac hypertrophy and heart failure. (Hilfiker-Kleiner D et al., Cardiovasc. Res., 53:460-69 (2002)). The increase of these cardio-protective markers indicates that plasma fractions such as PPF1 can reinvigorate genetic pathways that reduce cardiac hypertrophy. Data is mean±SEM, *p<0.05 Welch's t-test.

9. Example 9

Lactate is known to promote myoblast differentiation and myotube hypertrophy (See, e.g. Tsukamoto S et al., Int. J. Molec. Sci. 19:3649 (2018)). Thus, measuring lactate production in myoblasts can be an indicator of both differentiation and growth in muscle. C12C2 myoblasts were differentiated to myotubes for 5 days in vitro in 2% horse serum (HS) differentiation medium. At day 5, various treatments were added to the cells. Based on the assessed $EC_{50}$ values by glucose utilization the plasma fractions were added at 5 mg/mL to the media, except for IV-1 paste which was added at three different concentrations (0.25, 2.5, and 5 mg/mL). Also at day 5, positive control metformin was added (1 mM). At day 6, the cells were again treated with metformin and oligomycin (250 nM) as positive controls and 2-Deoxy-D-Glucose (2-DG, 100 nM) as negative control for either three (3) hours or five (5) hours (FIGS. 21A and 21B, respectively). After 3 or 5 hours, the media was deproteinized and subsequently, the amount of lactate produced was measured by an enzymatic reaction.

FIG. 21A shows the amount of lactate (a myogenic differentiating factor) produced in C2C12 cells in response to three (3) hours of treatment with various factors. These included vehicle, 2-DG (negative control), metformin (positive control), oligomycin, HAS1, recombinant human albumin (rhAlbumin), PPF1, fraction IV-1 paste suspension, and three different concentrations of fraction IV-1 paste suspension. Data was from two wells each from three independent experiments ±SEM. This data shows that after 3 hours of treatment: HAS1 and rhAlbumin exhibited no increase in lactate production over untreated control; PPF1 showed a very slight trend in increased lactate production; and fraction IV-4 and IV-1 paste suspensions exhibited a distinct increase in lactate production. Data n=2 wells from three independent experiments ±SEM ****p<0.0001 nested one-way ANOVA. Lactate production did not correlate entirely with glucose utilization with plasma fractions and this suggests that plasma fractions induce different mechanisms in the cells.

FIG. 21B shows the effects on lactate production on C2C12 cells after five (5) hours of treatment with the various factors described in FIG. 21A. Data was from two wells each from two independent experiments ±SEM. This data shows that after 5 hours of treatment: HAS1 and rhAlbumin exhibited no increase in lactate production over untreated control; PPF1 showed a trend in increased lactate production; and fraction IV-4 and IV-1 paste suspensions exhibited a distinct increase in lactate production. Data n=2 wells from two independent experiments ±SEM ****p<0.0001 nested one-way ANOVA.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The invention claimed is:

1. A method of improving muscle regeneration thereby reducing symptoms of a muscle disorder in a subject diagnosed with the muscle disorder, the method comprising administering an effective amount of a Plasma Fraction to the subject wherein the Plasma Fraction is a Plasma Protein Fraction (PPF) containing between 83% and 95% albumin, no more than 17% globulin and no more than 1% gamma globulin.

2. The method of claim 1 wherein the administering is performed using a Pulse Dose dosing regimen.

3. The method of claim 1 wherein the muscle disorder resulted from acute injury.

4. The method of claim 1 wherein the muscle disorder is a dystrophy.

5. The method of claim 4 wherein the dystrophy is selected from the group consisting of Duchenne and Becker muscular dystrophy, myotonic dystrophy, limb girdle muscular dystrophy, Emery-Dreifuss muscular dystrophy, congenital muscular dystrophy, and facioscapulohumeral muscular dystrophy.

6. The method of claim 1 wherein the muscle disorder is selected from the group consisting of muscle atrophy, muscle weakness, McArdle disease, muscle weakness associated with stroke, degeneration associated with amyotrophic lateral sclerosis, neuromuscular junction disorders, myasthenia gravis, toxic myopathy, inflammatory myopathy, lipid storage myopathy, ischemia, and contraction-induced damage.

7. The method of claim 1 wherein the muscle disorder is acute muscle injury resulting from sports activity.

8. The method of claim 1 wherein reducing symptoms of the muscle disorder comprises eliminating symptoms of the muscle disorder.

* * * * *